(12) United States Patent
Hayashi et al.

(10) Patent No.: US 12,036,004 B2
(45) Date of Patent: Jul. 16, 2024

(54) PHYSIOLOGICAL STATE INDEX CALCULATION SYSTEM, PHYSIOLOGICAL STATE INDEX CALCULATION METHOD, AND NON-TRANSITORY COMPUTER READABLE MEDIUM

(71) Applicant: TOYOTA JIDOSHA KABUSHIKI KAISHA, Toyota (JP)

(72) Inventors: Keiji Hayashi, Toyota (JP); Hitoshi Yamada, Toyota (JP); Yuhei Yamaguchi, Nagoya (JP); Chie Imamura, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 140 days.

(21) Appl. No.: 17/969,829

(22) Filed: Oct. 20, 2022

(65) Prior Publication Data

US 2023/0148873 A1 May 18, 2023

(30) Foreign Application Priority Data

Nov. 18, 2021 (JP) ................................. 2021-187848

(51) Int. Cl.
*A61B 5/02* (2006.01)
*A61B 5/022* (2006.01)
*G01R 23/165* (2006.01)

(52) U.S. Cl.
CPC .............. *A61B 5/02* (2013.01); *G01R 23/165* (2013.01); *A61B 5/02225* (2013.01)

(58) Field of Classification Search
CPC ..... A61B 5/02; A61B 5/02225; A61B 5/0022; A61B 5/165; A61B 5/7246; A61B 5/7257; A61B 5/7225; A61B 5/4064; A61B 5/0261; A61B 5/026; G01R 23/165
See application file for complete search history.

(56) References Cited

U.S. PATENT DOCUMENTS

| | | | | |
|---|---|---|---|---|
| 5,995,868 | A * | 11/1999 | Dorfmeister | A61N 1/36135 600/545 |
| 11,763,665 | B2 * | 9/2023 | Gopalakrishnan | A61B 5/02055 600/301 |
| 2007/0060785 | A1 * | 3/2007 | Freeman | A61H 31/006 600/16 |

(Continued)

FOREIGN PATENT DOCUMENTS

WO 2018/056137 A1 3/2018

*Primary Examiner* — Jermele M Hollington
*Assistant Examiner* — Zannatul Ferdous
(74) *Attorney, Agent, or Firm* — Oliff PLC

(57) ABSTRACT

A physiological state index calculation system, a physiological state index calculation method, and a non-transitory computer readable medium for capturing subtle changes in a physiological state of a living body are provided. The physiological state index calculation system includes a band-pass filter that filters cerebral blood flow waveform information obtained from a cerebral blood flow of a living body in at least one frequency band, and a complex number conversion unit configured to convert the filtered cerebral blood flow waveform information into a complex number for at least one frequency band. The cerebral blood flow waveform information converted into a complex number by the complex number conversion unit is an oscillator that reflects a physiological state of a living body.

11 Claims, 26 Drawing Sheets

(56) References Cited

U.S. PATENT DOCUMENTS

2019/0223830 A1* 7/2019 Thorpe .................. A61B 8/488
2020/0107812 A1* 4/2020 Wang ....................... A61B 8/06

* cited by examiner

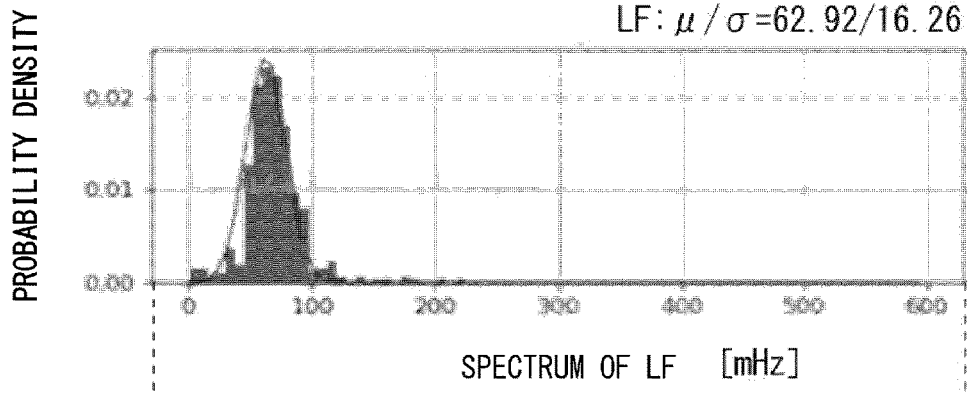
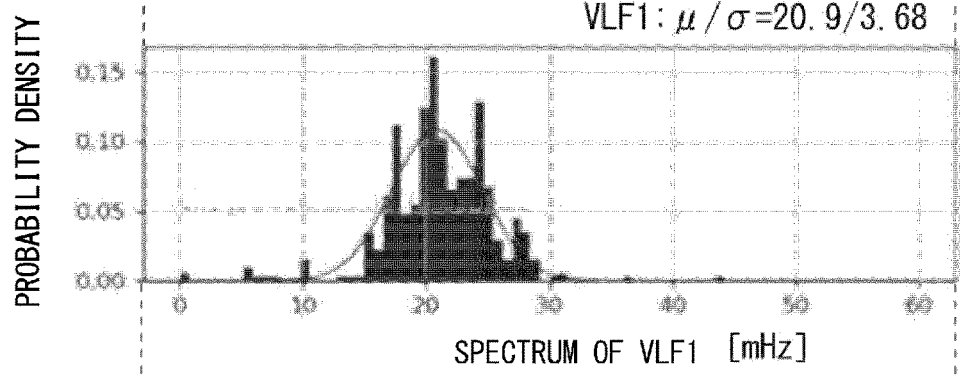
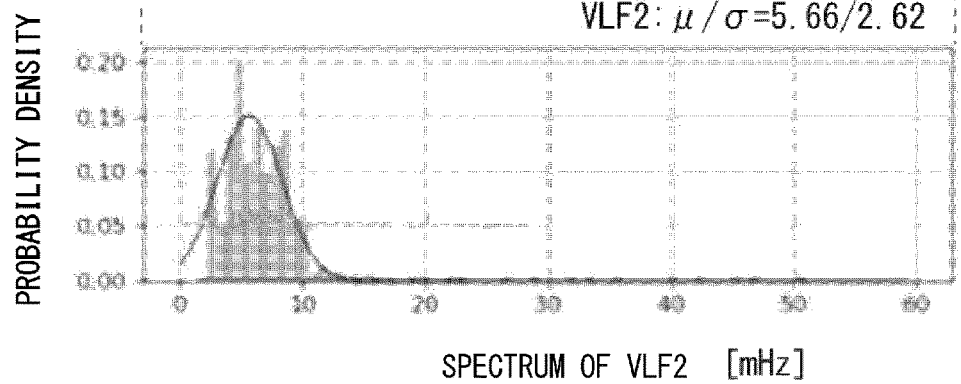
Fig. 5

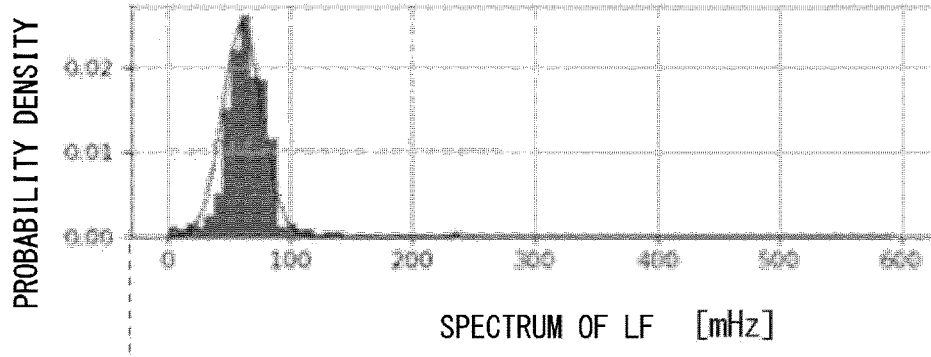
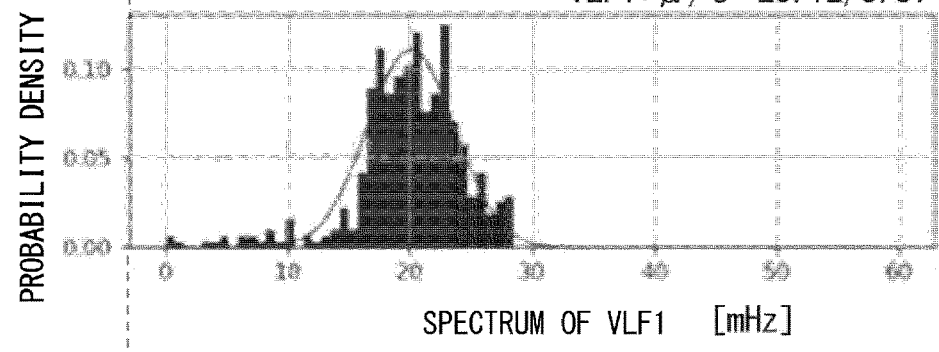
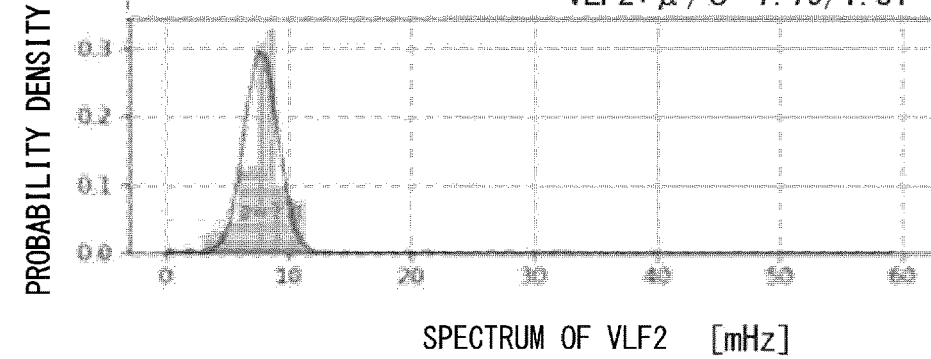
Fig. 7

| FEATURE AMOUNT | | | F VALUE OF ONE-WAY ANALYSIS OF VARIANCE OF ri LEVEL | F VALUE OF TWO-WAY ANALYSIS OF VARIANCE OF LEVEL OF ri+id |
|---|---|---|---|---|
| AVERAGE $\mu$ AND STANDARD DEVIATION $\sigma$ OF INSTANTANEOUS AMPLITUDE OF LEFT BRAIN | $\mu$ L F | m l 1 | | |
| | $\sigma$ L F | s l 1 | | |
| | $\mu$ V L F 1 | m v 1 | | |
| | $\sigma$ V L F 1 | s v 1 | | |
| | $\mu$ V L F 2 | m w 1 | 0.0882 | 0.0484 |
| | $\sigma$ V L F 2 | s w 1 | 0.0483 | 0.082 |
| AVERAGE $\mu$ AND STANDARD DEVIATION $\sigma$ OF INSTANTANEOUS FREQUENCY OF LEFT BRAIN | $\mu$ L F | m l f 1 | | |
| | $\sigma$ L F | s l f 1 | | |
| | $\mu$ V L F 1 | m v f 1 | | |
| | $\sigma$ V L F 1 | s v f 1 | | |
| | $\mu$ V L F 2 | m w f 1 | | |
| | $\sigma$ V L F 2 | s w f 1 | 0.0876 | 0.0581 |
| AVERAGE $\mu$ AND STANDARD DEVIATION $\sigma$ OF INSTANTANEOUS AMPLITUDE OF RIGHT BRAIN | $\mu$ L F | m l 2 | | |
| | $\sigma$ L F | s l 2 | | |
| | $\mu$ V L F 1 | m v 2 | | |
| | $\sigma$ V L F 1 | s v 2 | | |
| | $\mu$ V L F 2 | m w 2 | 0.0125 | 0.0126 |
| | $\sigma$ V L F 2 | s w 2 | | |
| AVERAGE $\mu$ AND STANDARD DEVIATION $\sigma$ OF INSTANTANEOUS FREQUENCY OF RIGHT BRAIN | $\mu$ L F | m l f 2 | | |
| | $\sigma$ L F | s l f 2 | | |
| | $\mu$ V L F 1 | m v f 2 | | |
| | $\sigma$ V L F 1 | s v f 2 | | |
| | $\mu$ V L F 2 | m w f 2 | | |
| | $\sigma$ V L F 2 | s w f 2 | | |

Fig. 9

|  | m w 1 | s w 1 | s w f 1 | m w 2 |
|---|---|---|---|---|
| VAS | 0.0972 |  | 0.096 |  |
| pleasant | 0.0262 | 0.011 |  |  |
| arousal |  |  |  |  |
| sleepy |  |  |  |  |
| active_ |  |  |  |  |
| relax_ | 0.00951 | 0.00366 |  |  |
| strainR |  |  |  |  |
| concentrate |  |  |  |  |
| motivation |  |  |  |  |
| fatigue |  |  | 0.07847 |  |
| pleasantP_ |  |  |  |  |
| angry |  |  |  |  |
| anxiety |  | 0.0281 | 0.0489 |  |
| stress | 0.0366 |  | 0.0835 |  |
| strainP |  |  |  |  |
| res_m | 0.0487 |  |  |  |
| res_s | 0.0198 |  |  |  |

Fig. 14

| | m w 1 | s w 1 | s w f 1 | m w 2 |
|---|---|---|---|---|
| VAS | ↑ | | ↑ | |
| pleasant | ↓ | ↓ | | |
| arousal | | | | |
| sleepy | | | | |
| active_ | | | | |
| relax_ | ↑ | ↑ | | |
| strainR | | | | |
| concentrate | | | | |
| motivation | | | | |
| fatigue | | | ↑ | |
| pleasantP_ | | | | |
| angry | | | | |
| anxiety | | ↓ | ↑ | |
| stress | ↑ | | ↑ | |
| strainP | | | | |
| res_m | ↓ | | | |
| res_s | ↓ | | | |

↑ : POSITIVE CORRELATION
↓ : NEGATIVE CORRELATION

Fig. 15

PHYSIOLOGICAL STATE INDEX CALCULATION SYSTEM, PHYSIOLOGICAL STATE INDEX CALCULATION METHOD, AND NON-TRANSITORY COMPUTER READABLE MEDIUM

CROSS REFERENCE TO RELATED APPLICATIONS

This application is based upon and claims the benefit of priority from Japanese patent application No. 2021-187848, filed on Nov. 18, 2021, the disclosure of which is incorporated herein in its entirety by reference.

BACKGROUND

The present disclosure relates to a physiological state index calculation system, a physiological state index calculation method, and a non-transitory computer readable medium for calculating physiological state indices of a living body.

In related art, various techniques for calculating physiological state indices of a living body have been proposed. As an example of these techniques, a disease condition determination apparatus disclosed in International Patent Publication No. WO 2018/056137 determines a disease condition of a subject based on a degree of separation of two kinds of blood flow information based on loads different from each other, amplitude of a change in a hemoglobin concentration of a cerebral blood flow, and a phase of the change in the hemoglobin concentration of the cerebral blood flow.

SUMMARY

There is a problem in the disease condition determination apparatus disclosed in International Patent Publication No. WO 2018/056137 that it is impossible to capture subtle changes in the physiological state of a subject since this disease condition determination apparatus statistically processes the amplitude and the phase, which are directly detected from a change in the amount of the cerebral blood flow from a subject to which two types of load tasks are given, and determines a disease condition based on the magnitude of the change in the amount of the cerebral blood flow.

The present disclosure has been made in order to solve the aforementioned problem and an object of the present disclosure is to provide a physiological state index calculation system, a physiological state index calculation method, and a non-transitory computer readable medium storing a physiological state index calculation program for capturing subtle changes in a physiological state of a living body.

A physiological state index calculation system configured to calculate a physiological state index of a living body according to one aspect of the present disclosure includes:
  a waveform information generation unit configured to measure a cerebral blood flow of a living body, which is time series data, in at least one part of a brain to generate blood flow amount waveform information; and
  a band-pass filter configured to filter the blood flow amount waveform information in at least one frequency band and an arithmetic unit configured to convert the filtered blood flow amount waveform information into a complex number.

The arithmetic unit may obtain a logarithmic value of blood flow amount waveform information converted into the complex number as one oscillator for at least one frequency band, and the real part of this logarithmic value may be an instantaneous amplitude, the imaginary part of the logarithmic value may be an instantaneous phase, and the time differential value thereof may be an instantaneous frequency.

The arithmetic unit is further able to aggregate the instantaneous amplitude during a period in which the living body can be regarded as being in a physiologically steady state to calculate a probability distribution. This distribution becomes a monomodal distribution such as a Gaussian distribution. If the instantaneous frequency is aggregated to calculate the probability distribution, this distribution becomes a monomodal distribution such as a Gaussian distribution.

Last, the arithmetic unit is able to calculate an average value, a variance and the like from the monomodal distribution shapes of the instantaneous amplitude and the instantaneous frequency by fitting. They serve as feature amounts representing the physiological state.

According to the aforementioned method, the number of frequency bands×the number of cerebral blood flow measurement parts×4 (two amplitudes+two frequencies) mathematically independent feature amounts can be obtained and the physiological state can thus be treated as a multi-dimensional data space. By performing analysis using this method for physiological experiments, subtle changes in his/her physiological state, which have not been discerned in the physiological indices so far, can be statistically discerned.

Regarding the frequency band for performing band-pass filter, if tNIRS-1 non-invasive cerebral oxygen monitor C12707 (sampling frequency 0.2 Hz) manufactured by Hamamatsu Photonics K.K. is used, the physiological feature amount can be calculated in bands of 4-15 mHz (VLF2), 15-40 mHz (VLF1), and 0.04-0.15 Hz (LF).

Further, if NIRO-200NX manufactured by Hamamatsu Photonics K.K. is used, although the accuracy of the measurement of the cerebral blood flow is low, the sampling frequency is 20 Hz. Therefore, bands of 0.4-4 mHz (VLF2), 0.15-0.4 Hz (VLF1), 0.04-0.15 Hz (LF), 0.15-0.4 Hz (HF), 0.4-1.5 Hz ($\delta$1), 1.5-4 Hz ($\delta$2), and 4-8 Hz ($\theta$) are available. By using an apparatus having a high sampling frequency, the physiological feature amounts of a waves or larger of electroencephalogram can be calculated.

According to the present disclosure, it is possible to provide a physiological state index calculation system, a physiological state index calculation method, and a non-transitory computer readable medium storing a physiological state index calculation program for capturing subtle changes in a physiological state of a living body. More specifically, the cerebral blood flow waveform information converted into a complex number by a complex number conversion unit represents the physiological state of the living body using the distribution shapes of the instantaneous amplitude and the instantaneous frequency of each band waveform of the cerebral blood flow as feature amounts, whereby it is possible to capture subtle changes in a physiological state of a living body.

The above and other objects, features and advantages of the present disclosure will become more fully understood from the detailed description given hereinbelow and the accompanying drawings which are given by way of illustration only, and thus are not to be considered as limiting the present disclosure.

BRIEF DESCRIPTION OF DRAWINGS

FIG. 5 is a diagram showing one example of a distribution density of an instantaneous frequency $\omega_1k$ for each frequency band of the left frontal lobe of the subject;

FIG. 7 is a diagram showing one example of a distribution density of an instantaneous frequency $\omega_2k$ for each frequency band of the right frontal lobe of the subject;

FIG. 9 is a diagram showing results of an analysis of variance of feature amounts according to one aspect of the present disclosure;

FIG. 14 is a diagram showing results of a stepwise multiple regression analysis;

FIG. 15 is a diagram showing a correlation relation between objective variables (subjective indices and behavioral indices) and explanatory variables (feature amounts of physiological indices);

DESCRIPTION OF EMBODIMENTS

Fast Fourier Transform (FFT) Analysis of Cerebral Blood Flow Data

Figure 1:
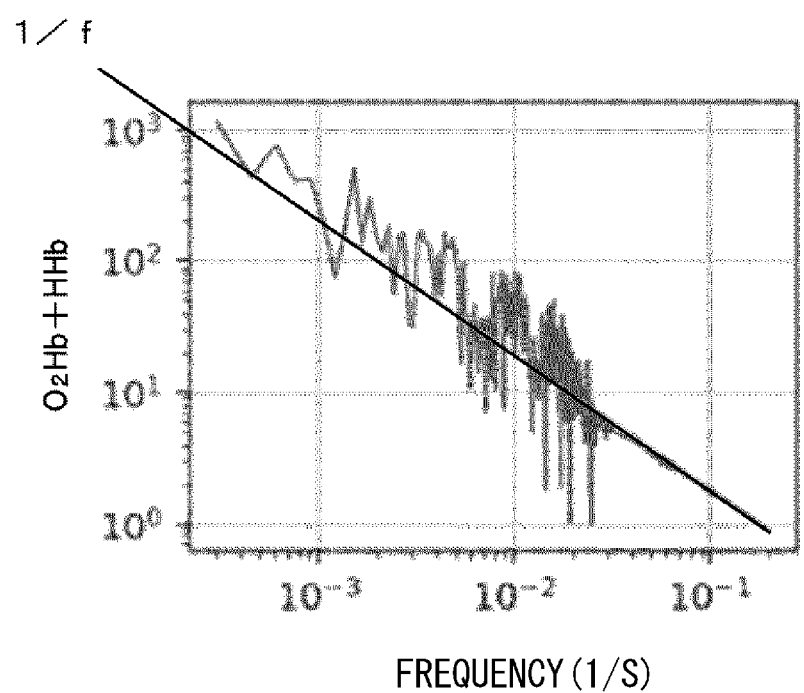
FIG. 1 is a diagram showing results of analyzing measurement data of a blood flow of a frontal lobe of a subject by FFT.

Hereinafter, with reference to the drawings, one aspect of the present disclosure will be described. FIG. 1 is a diagram showing results of measuring the blood flow of the frontal lobe of a subject using a non-invasive cerebral oxygen monitor (tNIRS-1 manufactured by Hamamatsu Photonics K.K.) and analyzing the measurement data by FFT. The sampling frequency at this time is 0.2 Hz and the measurement time is 60 minutes.

"$O_2Hb+HHb$" shown in FIG. 1, which represents the sum of an oxygenerated hemoglobin concentration and a deoxygenerated hemoglobin concentration, corresponds to a total hemoglobin concentration. The total hemoglobin concentration is proportional to the amount of the blood flow that flows through arteries of the frontal lobe of a subject. It is seen from FIG. 1 that the frequency spectrum of the total hemoglobin concentration ($O_2Hb+HHb$) is on the 1/f line.

Proposal of ak-ωk Analysis Method of Cerebral Blood Flow Data

Figure 2:
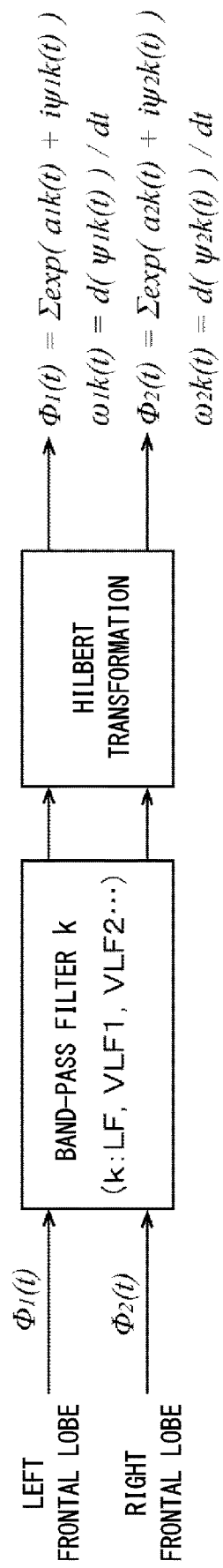
FIG. 2 is a diagram showing an algorithm according to one aspect of the present disclosure.

In one aspect of the present disclosure, an ak-ωk analysis method of measurement data of the total hemoglobin amount in the cerebral blood flow by a non-invasive cerebral oxygen monitor is proposed. In one aspect of the present disclosure, as shown in FIG. 2, waveform information indicating a total hemoglobin amount $\varphi1(t)$ in the cerebral blood flow of the left frontal lobe of the subject and a total hemoglobin amount $\varphi2(t)$ in the cerebral blood flow of the right frontal lobe of the subject that have been measured is subjected to band-pass filter processing in predetermined frequency bands. The predetermined frequency bands include, for example, a Low Frequency (LF) [0.04:0.15] Hz (blood pressure fluctuation), Very Low Frequency (VLF) 1 [15:40] mHz (first autonomic neurogenic fluctuation), and VLF2 [4:15] mHz (second autonomic neurogenic fluctuation). The LF is related to blood pressure fluctuation and VLF1 and VLF2 are related to autonomic neurogenic fluctuation.

Next, the waveform information in each frequency band is converted into a complex number. In this embodiment, Hilbert transformation is employed as a complex number conversion method. By converting the waveform information into a complex number in each frequency band, oscillation waveform expressions as shown in the following Equations 1 and 3 can be obtained. The symbol k represents each frequency band, like k=1 (VLF2), k=2 (VLF1), and k=3 (LF). Equations 1 and 2 are equations regarding the left brain. The real part $a_1k(t)$ of the logarithm in the oscillation waveform expression shown in Equation 1 represents the instantaneous amplitude and the imaginary part $\psi_1k(t)$ thereof represents an instantaneous phase. The part $\omega_1k(t)$ shown in Equation 2, which represents the instantaneous frequency, corresponds to a time differentiation of the instantaneous phase. Equations 3 and 4 are equations regarding the right brain. The real part $a_2k(t)$ of the logarithm in the oscillation waveform expression shown by Equation 3 represents the instantaneous amplitude and the imaginary part $\psi_2k(t)$ thereof represents an instantaneous phase. The symbol $\omega_2k(t)$ shown in Equation 4, which represents the instantaneous frequency, corresponds to a time differentiation of the instantaneous phase.

[Equation 1]

$$\Phi 1(t)=\Sigma \exp(a1k(t)+i\psi 1k(t)) \qquad (1)$$

[Equation 2]

$$\omega 1k(1)=d(\psi 1k(t))/dt \qquad (2)$$

[Equation 3]

$$\Phi 2(t)=\Sigma \exp(a2k(t)+i\psi 2k(t)) \qquad (3)$$

[Equation 4]

$$\omega 2k(t)=d(\psi 2k(t))/dt \qquad (4)$$

While Equations 1 and 2 show the cerebral blood flow in the left frontal lobe and Equations 3 and 4 show the cerebral blood flow in the right frontal lobe, it is possible to concurrently measure the cerebral blood flow of the temporal lobe, the parietal lobe, the occipital lobe other than the frontal lobe and perform similar analysis using a multi-channel non-invasive cerebral oxygen monitor.

Method of Processing Total Hemoglobin Waveform Data

Figure 3:
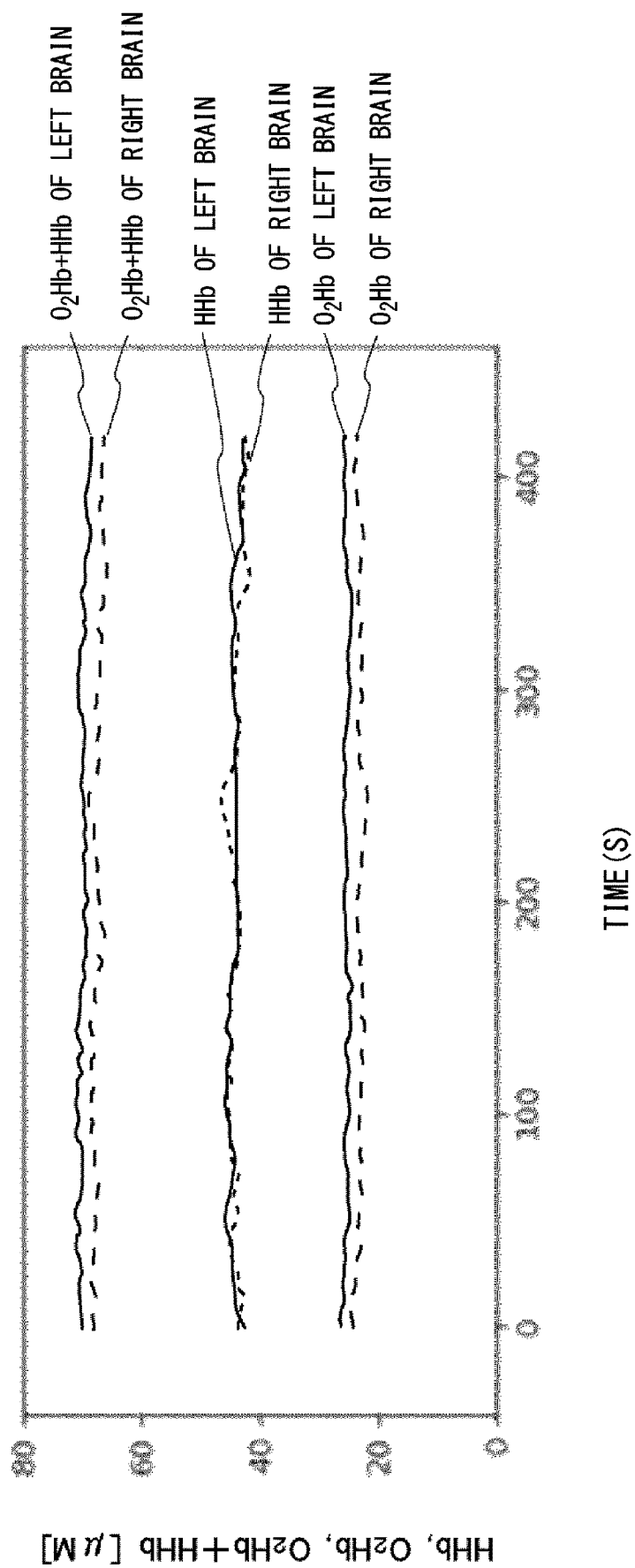
FIG. 3 is a diagram showing one example of a hemoglobin concentration in a blood flow of right and left frontal lobes of the subject.

FIG. 3 is a diagram showing the hemoglobin concentration in the blood flow of the right and left frontal lobes of the subject during a period in which the living body can be regarded as being in a physiologically steady state (hereinafter a "physiologically steady period"). In the example shown in FIG. 3, the physiologically steady period was set to seven minutes. In FIG. 3, the cerebral blood flow of the right and left frontal lobes of the subject was measured. FIG. 3 shows each of the first cerebral blood flow information (oxygenated hemoglobin concentration in the blood flow: $O_2Hb$), the second cerebral blood flow information (deoxygenated hemoglobin concentration: HHb), and the total hemoglobin concentration ($O_2Hb+HHb$), which is the total of them.

Figure 4:
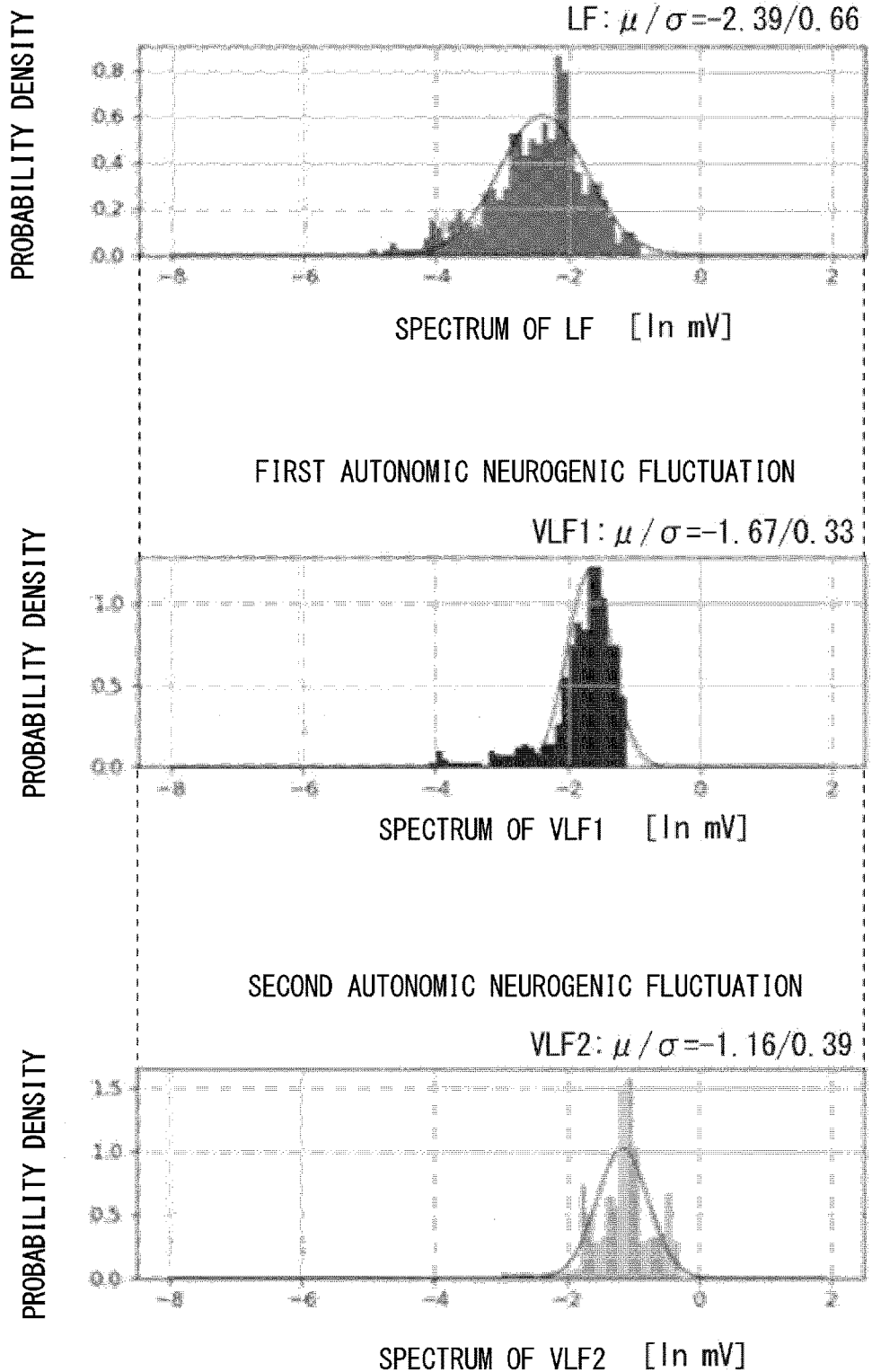
FIG. 4 is a diagram showing one example of a distribution density of an instantaneous amplitude $a_1k$ for each frequency band of the left frontal lobe of the subject.
Figure 6:
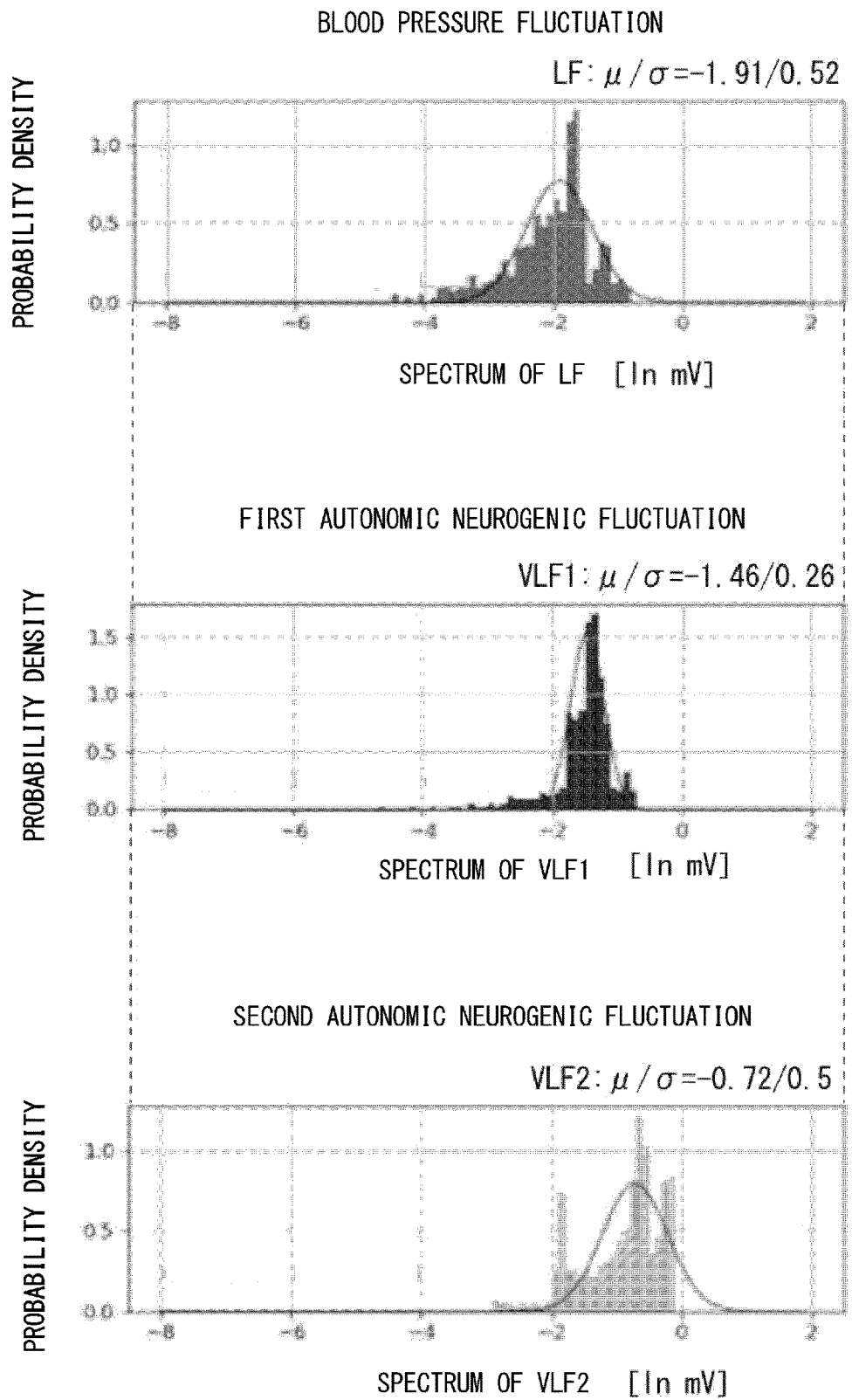
FIG. 6 is a diagram showing one example of a distribution density of an instantaneous amplitude $a_2k$ for each frequency band of the right frontal lobe of the subject.

As a result of deriving the aforementioned Equations 1-4 based on the data of the total of the oxygenated hemoglobin concentration and the deoxygenated hemoglobin concentration, aggregating the time series data shown in Equations 1-4 during the period in which the living body can be regarded as being in the physiologically steady state, and calculating the distribution densities, results shown in FIGS. 4-7 were obtained. The above Equations 1-4 may be derived based on one of data of the oxygenated hemoglobin concentration and data of the deoxygenated hemoglobin concentration. FIG. 4 is a diagram showing the distribution density (logarithm normal distribution) of the instantaneous amplitude $a_1k$ in the frequency bands (LF, VLF1, and VLF2) of the left frontal lobe of the subject. FIG. 5 is a diagram showing the distribution density (normal distribution) of the instantaneous frequency $\omega_1k$ in the frequency bands (LF, VLF1, and VLF2) of the left frontal lobe of the subject. FIG. 6 is a diagram showing the distribution density (logarithm normal distribution) of the instantaneous amplitude $a_2k$ in the frequency bands (LF, VLF1, and VLF2) of the right frontal lobe of the subject. FIG. 7 is a diagram showing the distribution density (normal distribution) of the instantaneous frequency $\omega_2k$ in the frequency bands (LF, VLF1, VLF2) of the right frontal lobe of the subject. As shown in FIGS. 4-7, the distribution densities of the time series data shown in Equations 1-4 can be approximated by a Gaussian distribution.

Feature amounts representing the physiologically stable state of the subject in the aforementioned measurement period may be obtained by fitting the distribution densities of the instantaneous amplitude $a_1k$, the instantaneous amplitude $a_2k$, the instantaneous frequency $\omega_1k$, and the instantaneous frequency $\omega_2k$ by a normal distribution (solid line in the drawings) and calculating the average and the standard deviation of the distribution.

By using a non-invasive cerebral oxygen monitor such as NIRO-200NX (sampling frequency 20 Hz) manufactured by Hamamatsu Photonics K.K. in which the upper limit of the sampling frequency is higher than that of the non-invasive cerebral oxygen monitor used in this experiment, High Frequency (HF) [0.15:0.4] Hz band, δ [0.4:1.5] Hz, θ [1.5:4] Hz, α [4:13] Hz bands may also be analyzed although the accuracy of the measurement is lower than that in the case in which the non-invasive cerebral oxygen monitor used in this experiment is employed. Further, if an apparatus having a high sampling frequency is used, physiological feature amounts equal to or larger than a waves can be calculated.

Further, if it is possible to hold the physiologically steady state for a long time (e.g., several tens of minutes) and measure the cerebral blood flow, a ULF band ([0.4:1.5] mHz, [1.5:4] mHz), which is further lower than the VLF band, may also be analyzed, and indices representing the state of the living body of, for example, an immune system, for a longer period may be derived.

The aforementioned description is based on a case in which the probability density distribution function for approximating the distribution is a normal distribution when it can be considered that the instantaneous amplitude $a_1k$ and the instantaneous frequency $\omega_1k$, (i=1, 2, . . . ) are in the physiologically steady state. However, the distribution is not limited to the normal distribution. This distribution may instead be approximated by other monomodal distributions such as a gamma distribution or a Lorentz distribution. When the distribution is approximated by a monomodal distribution other than the normal distribution, a shape parameter such as a variance value or a half-value width may be used in place of the standard deviation.

While the feature amounts are extracted by regarding the oscillation waveform, which is obtained by band-pass filtering one cerebral blood flow data piece and converting the filtered data piece into a complex number, as one oscillator in the aforementioned description, there is also a case in which a distribution is multimodal, which is a superposition of a plurality of oscillators. This case may include the following two cases, that is, a case in which the physiological state has been changed in a period in which the distributions are aggregated and a case in which there are a plurality of oscillators in the downstream of the arteries in the brain of the part to be measured. In the former case, the time interval for aggregating the distributions is divided to obtain a monomodal distribution. In the latter case, bandwidth to be band-pass filtered needs to be divided or the part to be measured needs to be moved to a downstream area of the arteries in the brain so that the distribution becomes monomodal as one oscillator.

Analysis of Cerebral Blood Flow Data in Fatigue Experiment

<Method of Experiment>

Figure 8:
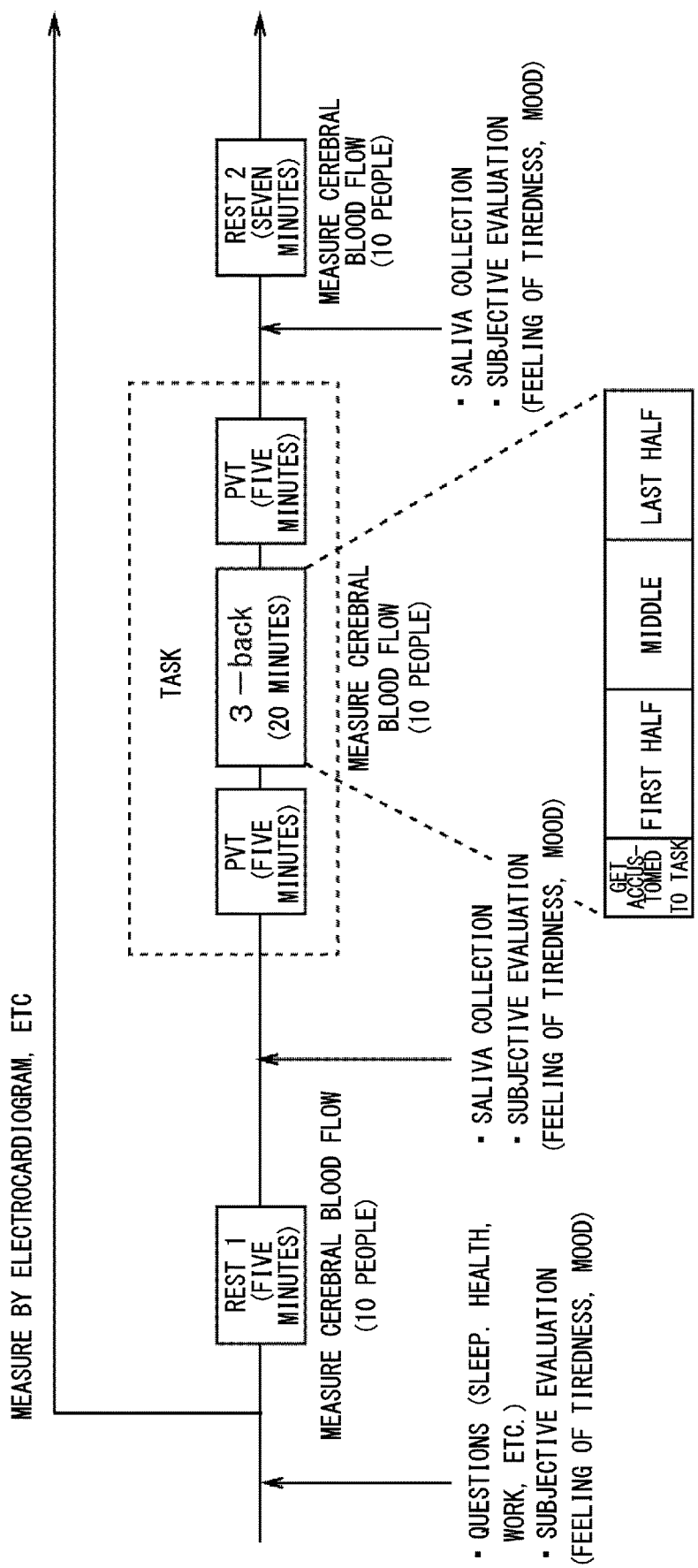
FIG. 8 is a diagram showing a protocol of a fatigue experiment conducted for subjects.

FIG. 8 is a diagram showing a protocol of a fatigue experiment conducted for 10 subjects. In order to evaluate the fatigue states of the subjects, as psychological indices, subjective evaluation such as tiredness and awakening subjective evaluation Roken Arousal Scale (RAS), or transient stress subjective evaluation Perceived Stress Scale (PSS) was conducted. Further, as behavioral indices, reaction time test Psychomotor Vigilance Task (PVT) was conducted before and after the fatigue task. Specifically, a 4-digit digital counter runs at random intervals of 2-10 seconds, and a reaction time to press the button on the hand of each subject to stop the movement of the counter was measured. Further, an N-back task (three-back, 20 minutes) was performed as the fatigue task. Further, as the physiological indices, the brain activity based on the cerebral blood flow was measured in the measurement in rest 1 and rest 2, and biochemical systems were measured by a salivary biomarker.

Subjects

The subjects were 10 healthy adult men, ranging in age from 20 to 44 years old, with a mean age was 28.5 years old.

<Design of Experiment>

For the purpose of searching objective indices regarding daily feeling of tiredness, a relation between the brain activity of the frontal lobe and the autonomic nerve activity before and after a fatigue load task, and results of subjective evaluation such as feeling of tiredness and task score of behavioral indices is considered. In this experiment, two meeting rooms were used, and two men or two women joined the experiments in each of the rooms. Each of the subjects participated in the experiment in one of the time schedule of 14:00-15:30 and 15:30-17:00. Measurement for five minutes in a sitting rest state (rest 1) was performed in a state in which each subject wears various electrodes and a non-invasive cerebral oxygen monitor (tNIRS-1 manufactured by Hamamatsu Photonics K.K., hereinafter, "NIRS") that measures the cerebral blood flow, and measurement for 10 minutes in a sitting rest state (rest 1) was performed in a state in which each subject does not wear the NIRS. Next, a task that will be described later was executed for a total of 30 minutes, and then measurement for seven minutes in a sitting rest state (rest 2) was performed. Until rest 2 for seven minutes is ended after the task, the right and left cerebral blood flow was measured in a state in which sensors of the NIRS apparatus were attached to the right and left forehead part of 10 men subjects. The environment of the experiment was adjusted in such a way that the room temperature was kept 25° C.±1° C. by changing the settings of air conditioners in the meeting rooms.

<Tasks and Behavioral Indices>

As a mental fatigue load task, using an n-back task, which is a working memory task in which the subjects answer whether the currently presented stimulus is the same as the stimulus presented n times before, 3-back task was performed on the subjects for 20 minutes (about 260 questions). Just before and just after the 3-back task, PVT was performed for five minutes. Regarding PVT, the score at the first PVT before the 3-back task was compared with the score at the second PVT after the 3-back task.

<Subjective Evaluation>

As a subjective evaluation, before and after the rest 1 and after the rest 2, feeling of tiredness was evaluated by Visual Analog Scale (VAS) and pleasant/unpleasant and awakening/drowsiness were evaluated by the affect grid method. Further, mood conditions related to tiredness and stress were evaluated using RAS and PSS.

<Measurement of Cerebral Blood Flow by Non-Invasive Cerebral Oxygen Monitor, ak-ωk Analysis, and Analysis of Variance>

The time series data of the total hemoglobin in the cerebral blood flow for five minutes (five minutes from the start) of each of rest 1 (five minutes) and rest 2 (one-six minutes) of 10 men whose cerebral blood flow was measured in rest 1 (five minutes), task, and rest 2 (seven minutes) was processed in the flow shown in FIG. 2, distribution densities of the instantaneous amplitude $a_1k$, the instantaneous frequency $\omega_1k$, the instantaneous amplitude $a_2k$, and the instantaneous frequency $\omega_2k$ were calculated, and these distribution densities were fit by a normal distribution. Accordingly, 24 feature amounts, that is, 2 (ak, ωk)×2 (left brain and right brain)×3 (LF, VLF1, VLF2)×2 (average μ, standard deviation σ), were obtained.

By performing, using the levels of ri (r1: rest 1, r2: rest 2) and id (10 subjects), analysis of variance (one-way analysis of variance of the level of ri and two-way analysis of variance of the level of ri+id) on these feature amounts, the results shown in FIG. 9 were obtained. Three feature amounts (mw1, sw1, mw2) where 95% significance was reached and one feature amount (swf1) where 90% significance was reached as a result of the task (five minutes of PVT+3-20 minutes of Back+five minutes of PVT) were extracted from the 24 feature amounts.

The feature amount mw1 is a feature amount representing the average u of the values of the instantaneous amplitude $a_1k$ in the complex number waveform expression of VLF2 derived from the total hemoglobin of the left brain frontal lobe of the subject. The feature amount sw1 is a feature amount representing the standard deviation σ of the values of the instantaneous amplitude $a_1k$ in the complex number waveform expression of VLF2 derived from the total hemoglobin of the left brain frontal lobe of the subject. The feature amount mw2 is a feature amount representing the average u of the values of the instantaneous amplitude $a_2k$ in the complex number waveform expression of VLF2 derived from the total hemoglobin of the right brain frontal lobe of the subject. The feature amount swf1 is a feature amount representing the standard deviation σ of the values of the instantaneous frequency $\omega_1k$, which is the time differential value of the instantaneous phase $\psi_1k$ in the complex number waveform expression of VLF2 derived from the total hemoglobin of the left brain frontal lobe of the subject.

The symbol "m" shown in FIG. 9 represents an average μ of the distribution. The symbol "s" represents a standard deviation σ of the distribution. The symbol "1" represents the amplitude of the LF band. The symbol "1f" represents the frequency of the LF band. The symbol "v" represents the amplitude of the VLF1 band. The symbol "vf" represents the frequency of the VLF1 band. The symbol "w" represents the amplitude of the VLF2 band. The symbol "wf" represents the frequency of the VLF2 band. The symbol "1" represents the left brain and the symbol "2" represents the right brain.

Figure 10:
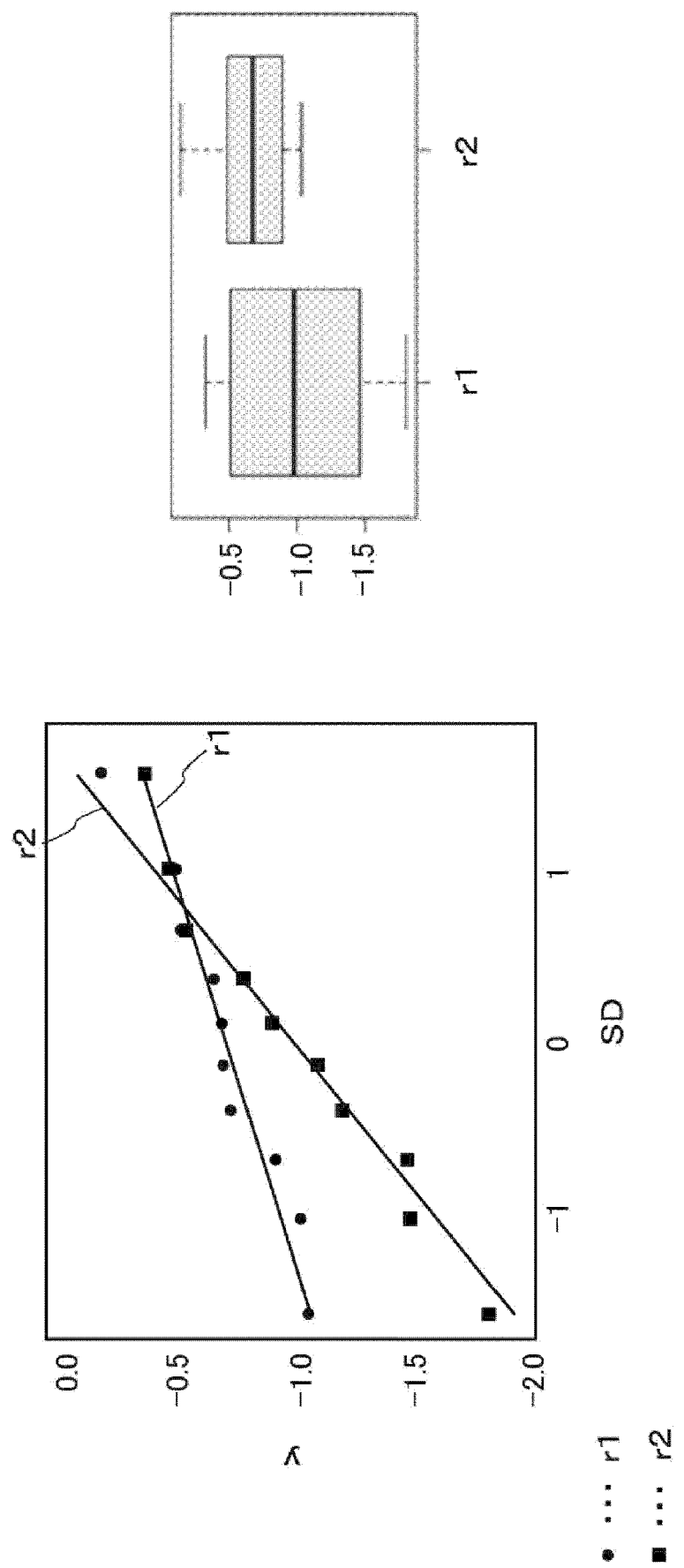
FIG. 10 shows a QQ plot and a box-and-whisker diagram of a feature amount mw1 according to one aspect of the present disclosure.
Figure 11:
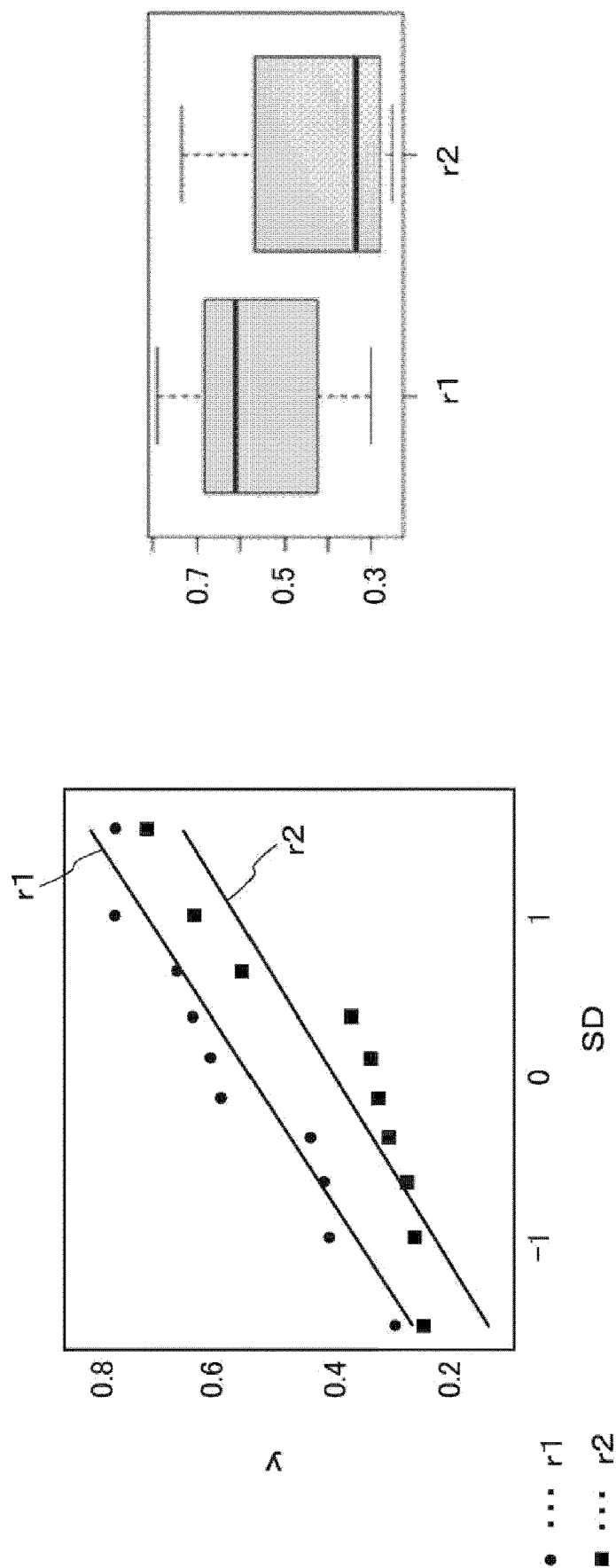
FIG. 11 shows a QQ plot and a box-and-whisker diagram of a feature amount sw1 according to one aspect of the present disclosure.
Figure 12:
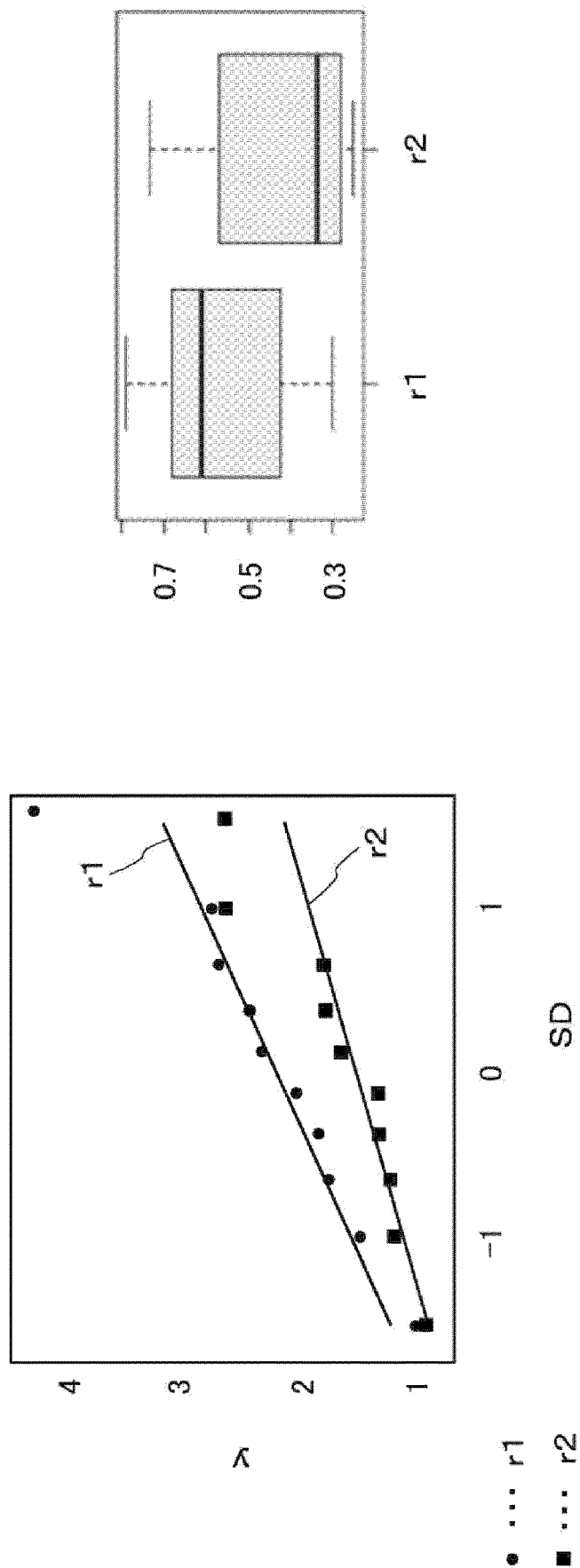
FIG. 12 shows a QQ plot and a box-and-whisker diagram of a feature amount swf1 according to one aspect of the present disclosure.
Figure 13:
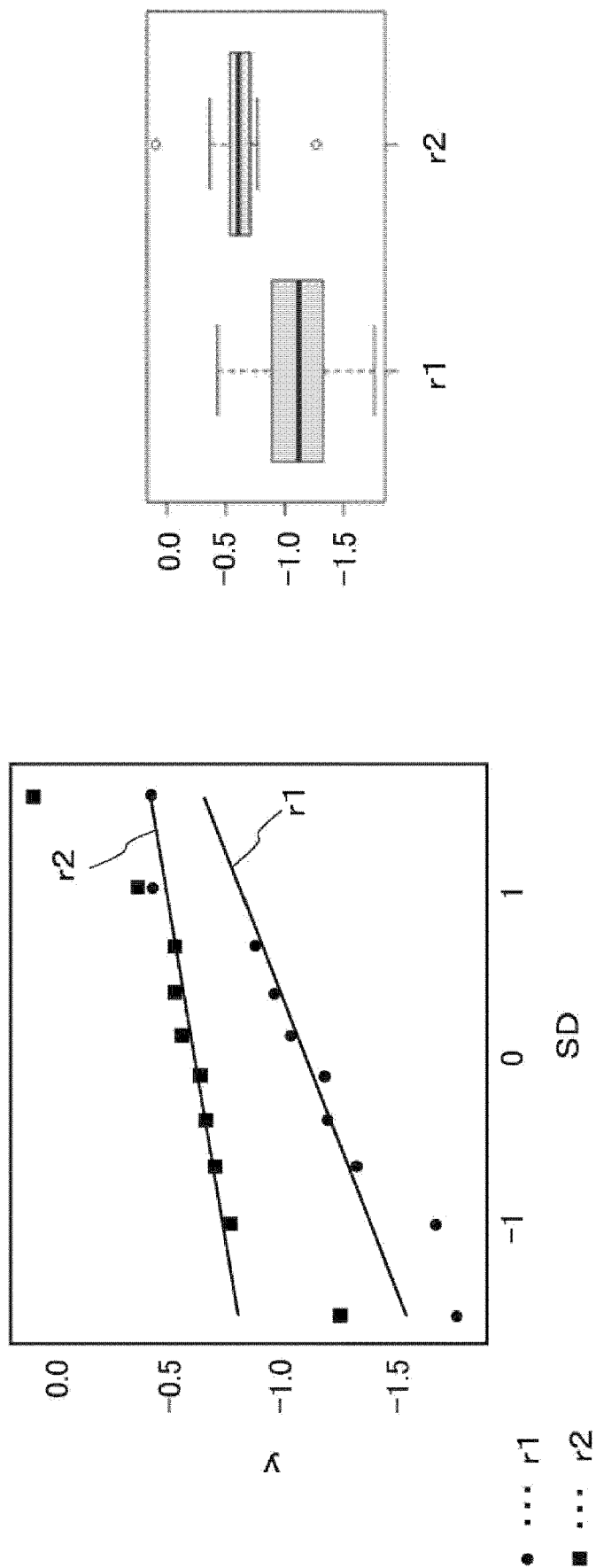
FIG. 13 shows a QQ plot and a box-and-whisker diagram of a feature amount mw2 according to one aspect of the present disclosure.

FIGS. 10-13 each show one-way analysis of variance before and after the fatigue task. FIG. 10 shows a QQ plot and a box-and-whisker diagram of the feature amount mw1 in each of rest 1 and rest 2. FIG. 11 shows a QQ plot and a box-and-whisker diagram of the feature amount sw1 in each of rest 1 and rest 2. FIG. 12 shows a QQ plot and a box-and-whisker diagram of the feature amount swf1 in each of rest 1 and rest 2. FIG. 13 shows a QQ plot and a box-and-whisker diagram of the feature amount mw2 in each of rest 1 and rest 2.

<Multiple Regression Analysis of Subjective Evaluation (RAS, PSS, VAS) and Behavioral Indices (PVT), and Feature Amounts of ak-ωk Analysis Method>

Multiple regression analysis has been performed using four feature amounts (mw1, sw1, swf1, mw2), which are physiological indices which have become significant as a result of the analysis of variance, as explanatory variables, and subjective indices (RAS, PSS, VAS, the affect grid (pleasant/unpleasant and awakening/drowsiness)) and the behavioral indices (PVT) as objective variables.

In order to reduce fluctuations in the subjective indices, the behavioral indices, and the feature amounts (mw1, sw1, swf1, mw2) of physiological indices in individuals, the difference between the subjective indices, the behavioral indices, and the feature amounts of the physiological indices before the task and those after the task was calculated, and stepwise multiple regression analysis was performed. Here, an operation of excluding explanatory variables in which p values exceed 10% as a result of the stepwise multiple regression and leaving only explanatory variables in which p values are equal to or lower than 10% was performed. FIG. 14 shows results of the stepwise multiple regression analysis. FIG. 15 shows a correlation relation between the objective variables (subjective indices and behavioral indices) and the explanatory variables (feature amounts of physiological indices).

The index VAS is an index indicating the strength of the tiredness expressed by a numerical value of 0-100. The indices pleasant (pleasantness) and arousal (awakening) are indices expressed by numerical values based on the affect grid. The indices sleepy (drowsiness), active_ (the opposite of active), relax_ (opposite of relaxed), strainR (nervous), concentrate (concentrated state), and motivation (motivated state) are indices which are based on the results of the response in RAS. The indices fatigue (weariness), Pleasant_P (unpleasant), angry (anger), anxiety (anxious), stress (stressed state), strainP (nervous) are indices which are based on the results of the response in PSS. The index res_m represents an average of the reaction time of PVT and res_s represents a standard deviation of a reaction time of PVT.

Figure 16:
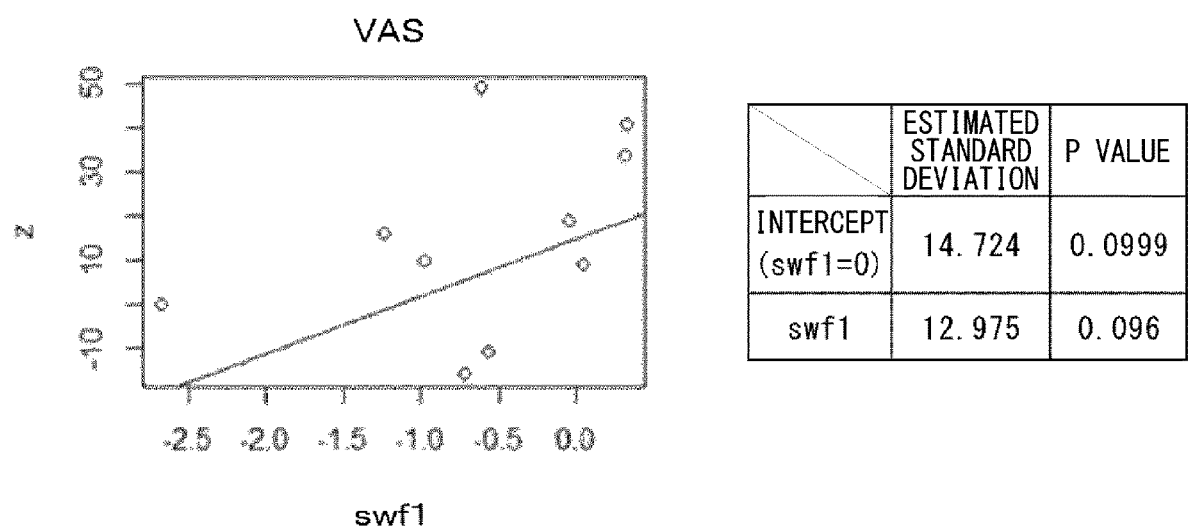
FIG. 16 is a diagram showing a correlation between VAS (feeling of tiredness) and the feature amount swf1 and a regression coefficient.
Figure 17:
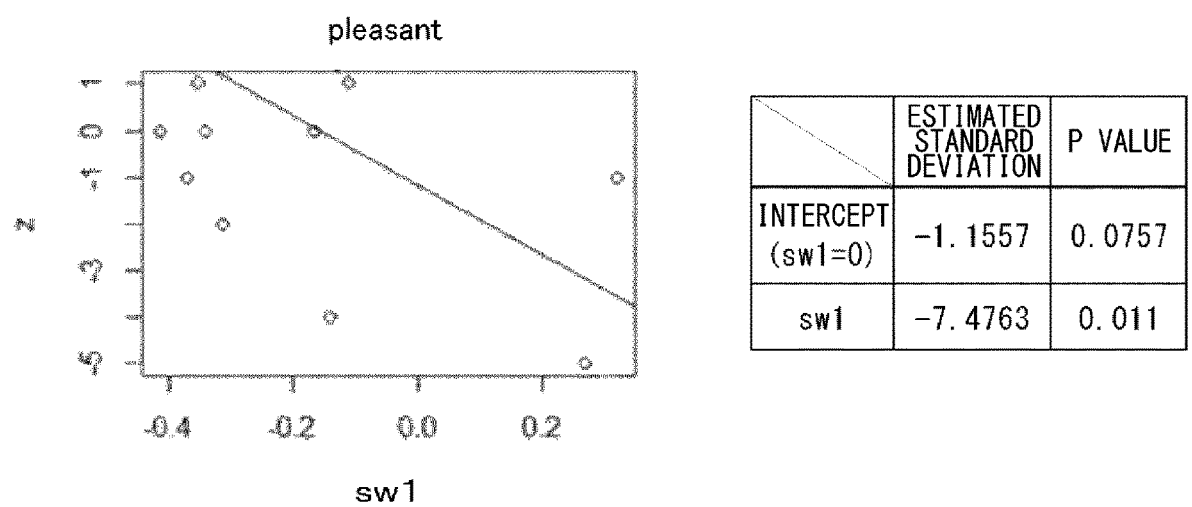
FIG. 17 is a diagram showing a correlation between pleasant (pleasantness) and the feature amount sw1 and a regression coefficient.
Figure 18:
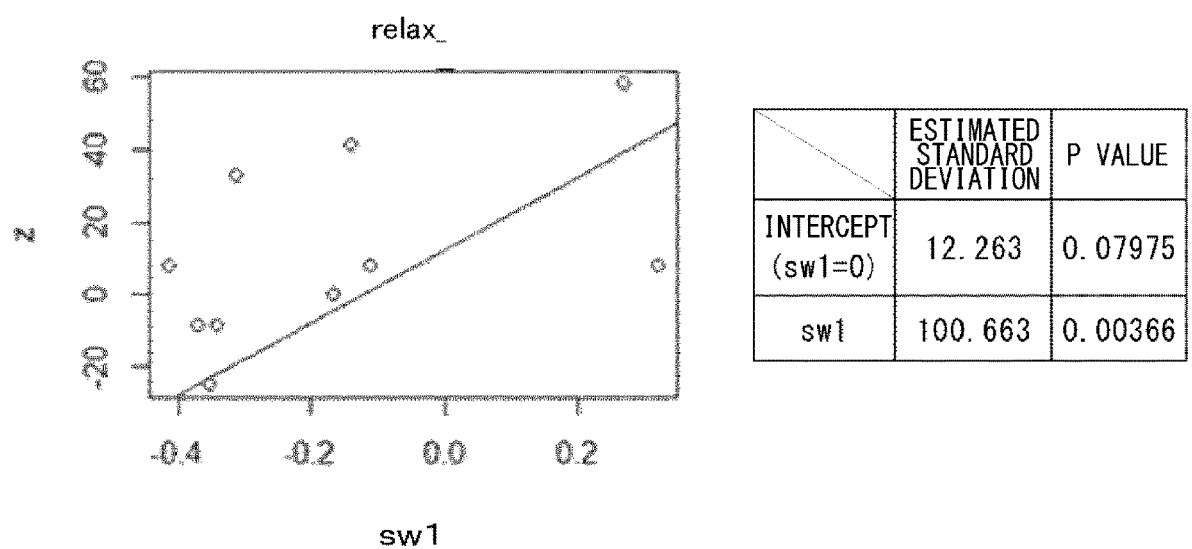
FIG. 18 is a diagram showing a correlation between relax_(opposite of relaxed) and the feature amount sw1 and a regression coefficient.
Figure 19:
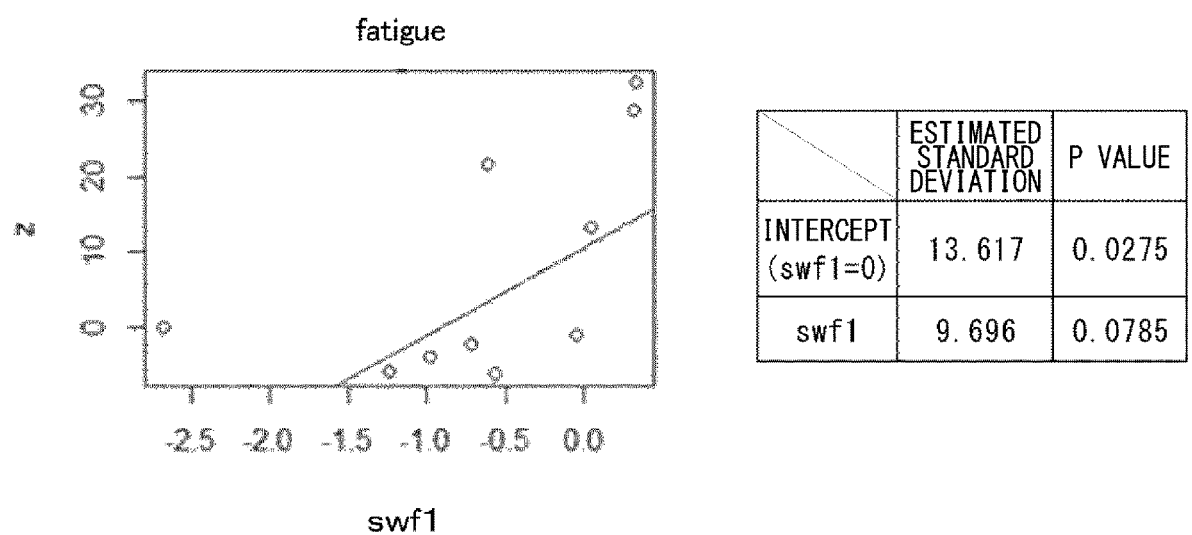
FIG. 19 is a diagram showing a correlation between fatigue (weariness) and the feature amount swf1 and a regression coefficient.
Figure 20:
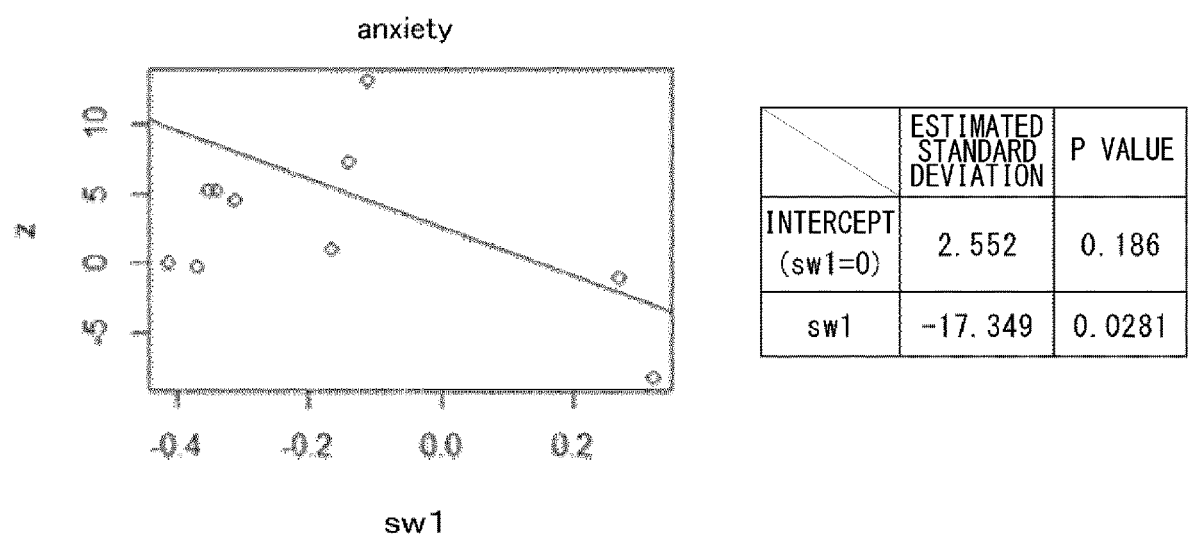
FIG. 20 is a diagram showing a correlation between anxiety (anxious) and the feature amount sw1 and a regression coefficient.
Figure 21:
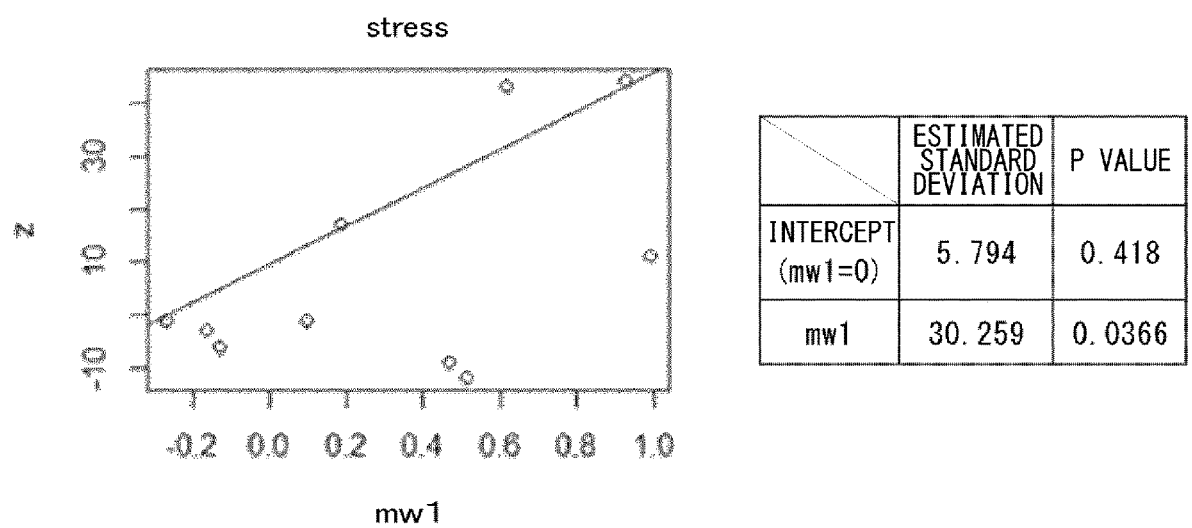
FIG. 21 is a diagram showing a correlation between stress (stressed) and feature amount mw1 and a regression coefficient.
Figure 22:
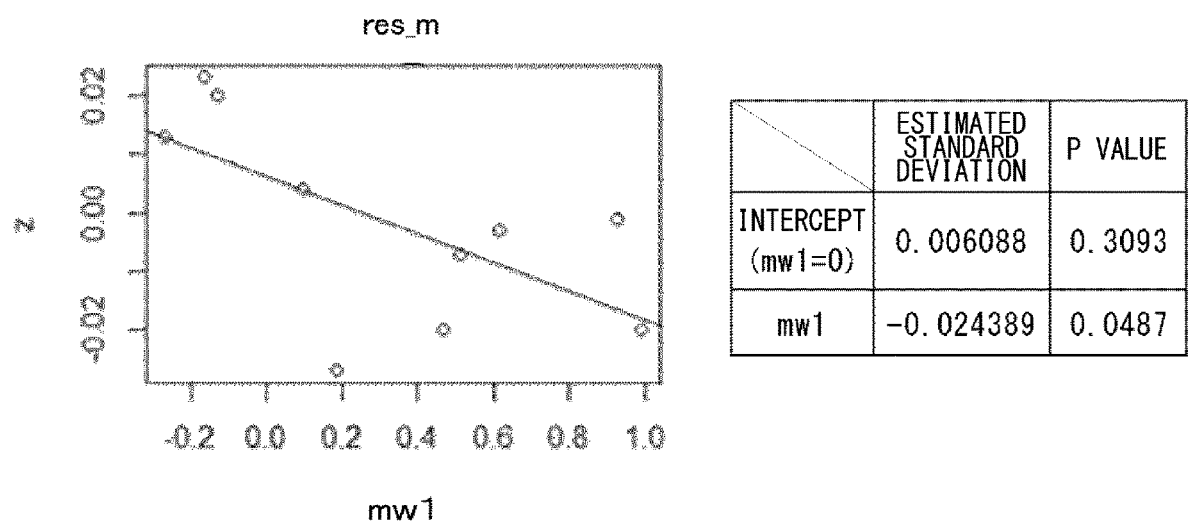
FIG. 22 is a diagram showing a correlation between res_m (an average of a reaction time of PVT) and the feature amount mw1 and a regression coefficient.
Figure 23:
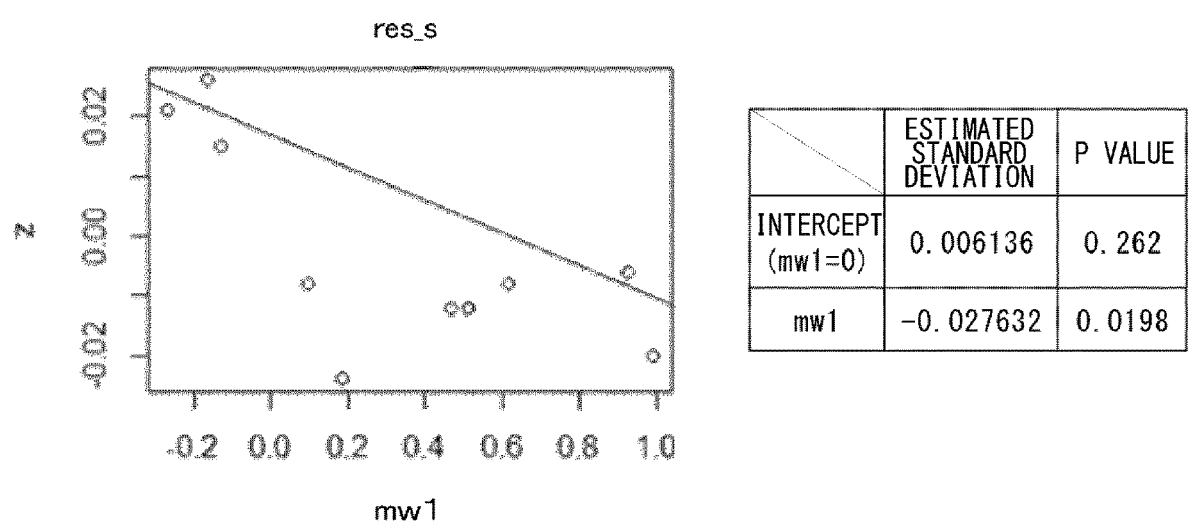
FIG. 23 is a diagram showing a correlation between res_s (a standard deviation of a reaction time of PVT) and the feature amount mw1 and a regression coefficient.

FIGS. 16-23 show a correlation between each of the objective variables (subjective indices and behavioral indices) and explanatory variables (feature amounts of physiological indices) and a regression coefficient. FIG. 16 shows a correlation between VAS (feeling of tiredness) and the feature amount swf1 and a regression coefficient. FIG. 17 shows a correlation between pleasant (pleasantness) and the feature amount sw1 and a regression coefficient. FIG. 18 shows a correlation between relax_ (opposite of relaxed) and the feature amount sw1 and a regression coefficient. FIG. 19 shows a correlation between fatigue (weariness) and the feature amount swf1 and a regression coefficient. FIG. 20 shows a correlation between anxiety (anxious) and the feature amount sw1 and a regression coefficient. FIG. 21 shows a correlation between stress (stressed) and the feature amount mw1 and a regression coefficient. FIG. 22 shows a correlation between res_m (average of a reaction time of PVT) and the feature amount mw1 and a regression coefficient. FIG. 23 shows a correlation between res_s (a standard deviation of the reaction time of PVT) and the feature amount mw1 and a regression coefficient.

It is seen from FIG. 15 that the feature amount swf1 (fluctuation in the frequency in the VLF2 band of the left forehead part) increases as VAS (tiredness), fatigue (weariness), anxiety (anxious), and stress (stressed) increase. It is further seen that the feature amount mw1 (the frequency average value in the VLF2 band of the left forehead part) increases as VAS (tiredness), relax_(opposite of relaxed), and stress (stressed) increase and the feature amount mw1 increases as Pleasant (pleasantness) decreases. It seems opposite in terms of the fatigue effect that the feature amount mw1 increases as res_m (PVT reaction time average) and res_s (PVT reaction time standard deviation) decrease. However, it can be interpreted that those who seriously engaged in the PVT task had a faster reaction time but were fatigued as a result, whereas those who did not engage in the task seriously had a slower reaction time but were not fatigued. By performing the ak-ωk analysis in this manner, it was found that the increase in the tiredness appeared as the increase in the feature amount swf1 and the feature amount mw1.

Figure 24:
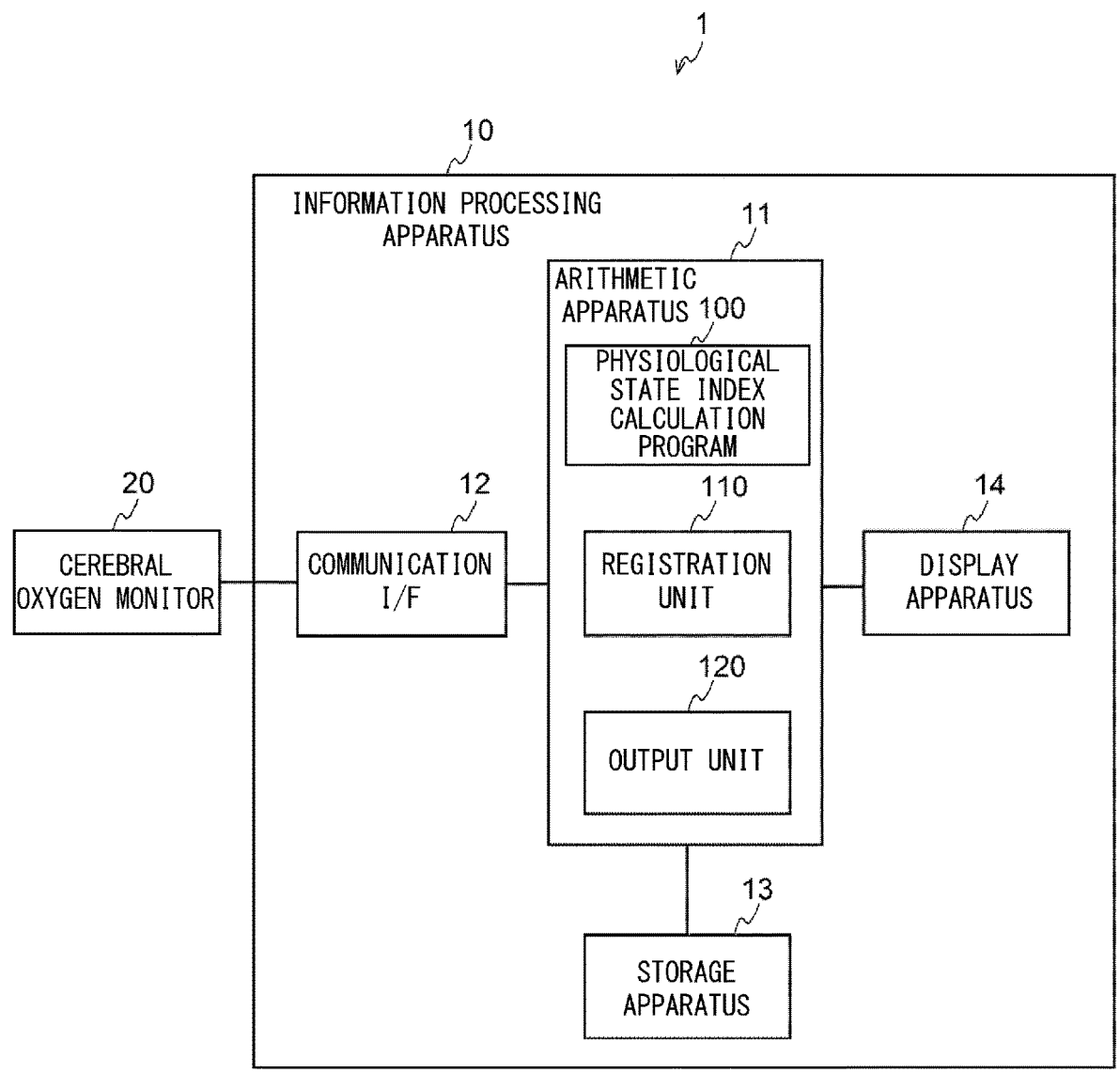
FIG. 24 is a diagram showing one example of a physiological state index calculation system according to one aspect of the present disclosure.

FIG. 24 shows one example of a physiological state index calculation system 1 according to one aspect of the present disclosure. The physiological state index calculation system 1 includes an information processing apparatus 10 and a cerebral oxygen monitor 20. Specific examples of the information processing apparatus 10 include a Personal Computer (PC), a server, a raspberry pi, a smartphone, a wearable terminal, a tablet terminal or the like. These apparatuses correspond to a computer.

Specific examples of the cerebral oxygen monitor 20 include the aforementioned tNIRS-1, NIRO-200NX or the like. Note that the function that the information processing apparatus 10 includes may be implemented in the cerebral oxygen monitor 20 and the physiological state index calculation system 1 may be formed as one apparatus.

The information processing apparatus 10 includes an arithmetic apparatus 11, a communication interface (I/F) 12, a storage apparatus 13, and a display apparatus 14.

The arithmetic apparatus 11 is an apparatus configured to control the entire information processing apparatus 10. Specific examples of the arithmetic apparatus 11 include a Central Processing Unit (CPU), a Micro Processing Unit (MPU), an Electronic Control Unit (ECU) or the like. The arithmetic apparatus 11 also corresponds to a computer.

The arithmetic apparatus 11 executes the physiological state index calculation program 100, the registration unit 110, and the output unit 120. The arithmetic apparatus 11 implements a physiological state index calculation method by executing the physiological state index calculation program. The details of the physiological state index calculation program 100 will be described later.

The registration unit 110 is a program for registering the physiological state indices that the physiological state index calculation program 100 has calculated in a database of the storage apparatus 13. The registration unit 110 may register the physiological state indices in a database constructed in an external apparatus.

The output unit 120 is a program for outputting the physiological state indices that the physiological state index calculation program 100 has calculated. The output unit 120 is able to output the physiological state indices to the display apparatus 14 to cause the display apparatus 14 to display the physiological state indices. Further, the output unit 120 is able to output the physiological state indices to an external apparatus via the communication interface 12.

Note that semiconductor devices such as a Field-Programmable Gate Array (FPGA) and an Application Specific Integrated Circuit (ASIC) may execute the physiological state index calculation program. These semiconductor devices also correspond to a computer.

The communication interface (I/F) 12 is an apparatus that communicates data with an external apparatus. The communication interface (I/F) 12 acquires cerebral blood flow information from the cerebral oxygen monitor 20. The communication interface (I/F) 12 is able to acquire the cerebral blood flow information from the cerebral oxygen monitor 20 connected to the communication interface (I/F) 12 via a dedicated line. Further, the communication interface (I/F) 12 may acquire the cerebral blood flow information from the cerebral oxygen monitor 20 via a network that can be formed of a Local Area Network (LAN) and/or a Wide Area Network (WAN).

The display apparatus 14 is an apparatus configured to display various kinds of information such as physiological state indices calculated by the arithmetic apparatus 11. The storage apparatus 13 is a storage apparatus that stores various kinds of information such as the physiological state index calculation program.

Figure 25:
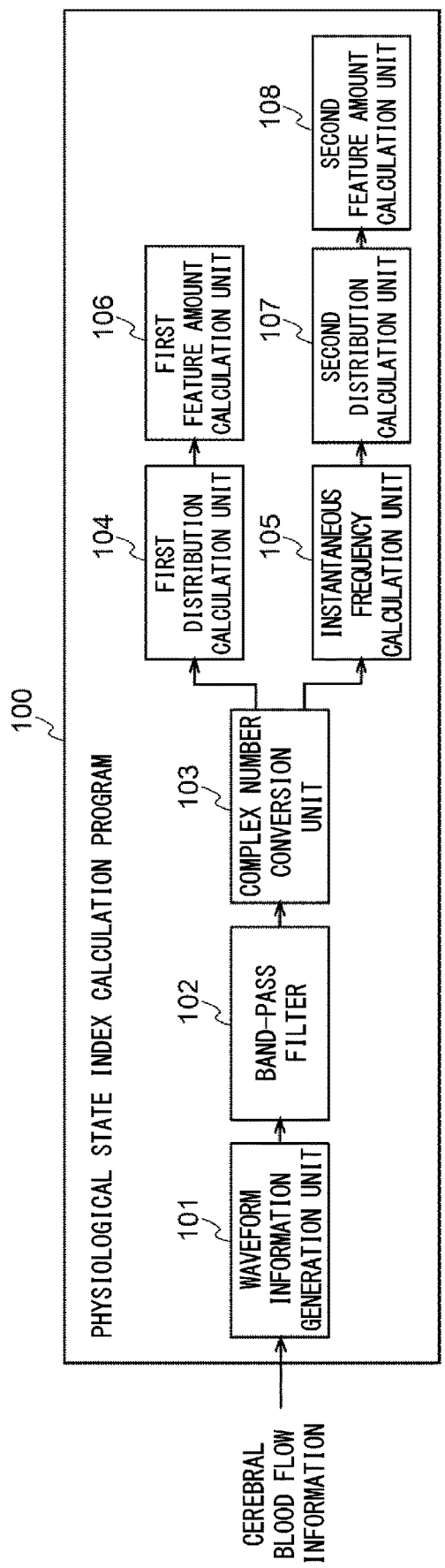
FIG. 25 is a diagram showing one example of a physiological state index calculation program according to one aspect of the present disclosure.

FIG. 25 is a diagram showing one example of the physiological state index calculation program 100. The physiological state index calculation program 100 generates the cerebral blood flow waveform information using at least one of cerebral blood flow information representing the amount of the blood flow of the left brain of the living body and cerebral blood flow information representing the amount of the blood flow of the right brain of the living body, which are time series data. Next, the physiological state index calculation program 100 filters the cerebral blood flow waveform information in at least one frequency band.

The physiological state index calculation program 100 calculates the logarithm of the converted waveform information which is the complex number, and aggregates the real part of the logarithm, which is an instantaneous amplitude, the imaginary part of the logarithm, which is an instantaneous phase, and the time differential value of the instantaneous phase, which is an instantaneous frequency, during a period in which the living body can be considered as being in a physiologically rest state. These distributions are like a Gaussian distribution. The physiological state index calculation program 100 approximates them with a normal distribution to calculate the average value μ and the standard deviation σ as physiological state indices of the living body. Specifically, the physiological state index calculation program 100 calculates, for the above predetermined frequency band, the instantaneous amplitude $a_i k(t)$ and the instantaneous frequency $\omega_i k(t)$ (i=1,2) of the complex equation in information on right and left cerebral blood flow waveforms in accordance with Equations (1)-(4), aggregates the instantaneous amplitude and the instantaneous frequency during a period in which the living body can be regarded as being in a physiologically steady state to calculate the probability density distribution, fits them by a normal distribution, and calculates the average value and the standard deviation for each band.

The physiological state index calculation program 100 includes a waveform information generation unit 101, a band-pass filter 102, a complex number conversion unit 103, a first distribution calculation unit 104, an instantaneous frequency calculation unit 105, a first feature amount calculation unit 106, a second distribution calculation unit 107, and a second feature amount calculation unit 108.

The waveform information generation unit 101 is a program configured to generate the cerebral blood flow waveform information using at least one of cerebral blood flow information representing the amount of the blood flow of the left brain of the living body and cerebral blood flow information representing the amount of the blood flow of the right brain of the living body, which are time series data. The cerebral blood flow information is obtained by measuring the blood flow at one or more parts of the body. Specific examples of the cerebral blood flow information include the concentration of the total hemoglobin, the oxygenerated hemoglobin concentration, or the deoxygenerated hemoglobin concentration in the intracerebral blood that reflects the amount of the blood flow in the brain of the living body. While the target brain regions are right and left frontal lobes in Examples, the target brain regions may be other brain regions such as a temporal lobe or an occipital lobe that may reflect the physiological state of the living body. Further, by measuring arteries that flow into the brain such as the internal carotid artery, the cerebral blood flow information may be obtained.

The band-pass filter 102 is a program for filtering the cerebral blood flow waveform information generated by the waveform information generation unit 101 in at least one frequency band. Specifically, the band-pass filter 102 divides the converted cerebral blood flow waveform information by a frequency band that can be regarded as at least one oscillator. This frequency band includes, for example, at least one of bands of 4-15 mHz (VLF2), 15-40 mHz (VLF1), and 0.04-0.15 Hz (LF). Further, the frequency band may include at least one of bands of 0.4-1.5 mHz (UHF2), 1.5-4 mHz (UHF1), 0.15-0.4 Hz (HF), 0.4-1.5 Hz (δ1 waves), 1.5-4 Hz (δ2 waves), 4-8 Hz (θ waves), 8-13 Hz (α waves), 13-30 Hz (β waves), and 30 Hz- (γ waves). Further, the band-pass filter 102 may divide, if a plurality of oscillators are found in the aforementioned frequency band, the aforementioned frequency band into a plurality of bands that correspond to these respective oscillators. Note that the frequency that corresponds to the boundary between the aforementioned frequency bands may be included in any band. For example, 15 mHz may belong to one of VLF1 and VLF2.

The cerebral blood flow waveform information includes first cerebral blood flow waveform information and second cerebral blood flow waveform information identified based on optical characteristics of blood. The band-pass filter 102 is able to filter cerebral blood flow waveform information obtained by adding the first cerebral blood flow waveform information and the second cerebral blood flow waveform information. Further, the band-pass filter 102 is able to filter one of the first cerebral blood flow waveform information and the second cerebral blood flow waveform information.

The complex number conversion unit 103 is a program for converting the cerebral blood flow waveform information filtered by the band-pass filter 102 into a complex number and generating the converted cerebral blood flow waveform information which is the complex number. Specifically, the complex number conversion unit 103 calculates the converted cerebral blood flow waveform information which is the complex number for the aforementioned predetermined frequency band. The complex number conversion unit 103 may employ, for example, Hilbert transformation as a complex number conversion method. Note that the complex number conversion method is not limited to Hilbert transformation and may be a desired complex number conversion method. The converted cerebral blood flow waveform information which is the complex number is an oscillator that reflects the physiological state of the living body.

The first distribution calculation unit 104 is a program for aggregating the real part of the logarithm in the oscillation waveform expression representing the cerebral blood flow waveform information converted into the complex number by the complex number conversion unit 103, which corresponds to the instantaneous amplitude, in a physiologically steady period to calculate a probability density distribution of the instantaneous amplitude. Specifically, the first distribution calculation unit 104 aggregates the real parts $a_1k(t)$ and $a_2k(t)$ of the logarithm shown by Equations 1 and 3 in the physiologically steady period to calculate the probability density distribution of the instantaneous amplitude. The distribution data is normally distributed like a Gaussian distribution.

The instantaneous frequency calculation unit 105 is a program for calculating the instantaneous frequency by obtaining the time differential value of the imaginary part of the logarithm in the oscillation waveform expression representing the cerebral blood flow waveform information converted into the complex number by the complex number conversion unit 103. The imaginary part of the logarithm in the oscillation waveform expression represents the instantaneous phase. Specifically, imaginary parts $\psi_1k(t)$ and $\psi_2k(t)$ of the logarithm shown by Equations 1 and 3 each represent the instantaneous phase. The instantaneous frequency calculation unit 105 calculates the instantaneous frequency by obtaining the time differential value of the imaginary parts $\psi_1k(t)$ and $\psi_2k(t)$ of the logarithm according to Equations 2 and 4. The instantaneous frequency may be used to calculate the time differential value.

The second distribution calculation unit 107 is a program for aggregating the instantaneous frequency calculated by the instantaneous frequency calculation unit 105 in a physiologically steady period to calculate the probability density distribution of the instantaneous frequency. The distribution data is normally distributed like a Gaussian distribution.

The first feature amount calculation unit 106 is a program that approximates a probability density distribution of the instantaneous amplitude calculated by the first distribution calculation unit 104 by a specific distribution and calculates at least one of the average value μ and the standard deviation σ of the specific distribution as a feature amount. The specific distribution includes a normal distribution and other distributions such as a gamma distribution or an exponential distribution. The first feature amount calculation unit 106 calculates a feature amount for each frequency band. The feature amounts calculated by the first feature amount calculation unit 106, that is, the average value and the standard deviation of the distribution of the instantaneous amplitude based on the right and left cerebral blood flow in the aforementioned frequency band, may be physiological state indices.

The second feature amount calculation unit 108 is a program that approximates the probability density distribution of the instantaneous frequency calculated by the second distribution calculation unit 107 by a specific distribution and calculates at least one of the average value μ and the standard deviation σ of the specific distribution as a feature amount. The specific distribution includes a normal distribution and other distributions such as a gamma distribution or an exponential distribution. The second feature amount calculation unit 108 calculates the feature amount for each frequency band. The feature amount calculated by the second feature amount calculation unit 108, that is, the average value and the standard deviation of the distributions of the instantaneous frequency based on the right and left cerebral blood flow in the above frequency band may be physiological state indices.

The output unit 120 outputs the average value and the standard deviation of the distributions of the instantaneous amplitude of the right and left cerebral blood flow in the above frequency band and the average value and the standard deviation of the distributions of the instantaneous frequency that have been calculated by the physiological state index calculation program 100 as the physiological state indices.

Figure 26:
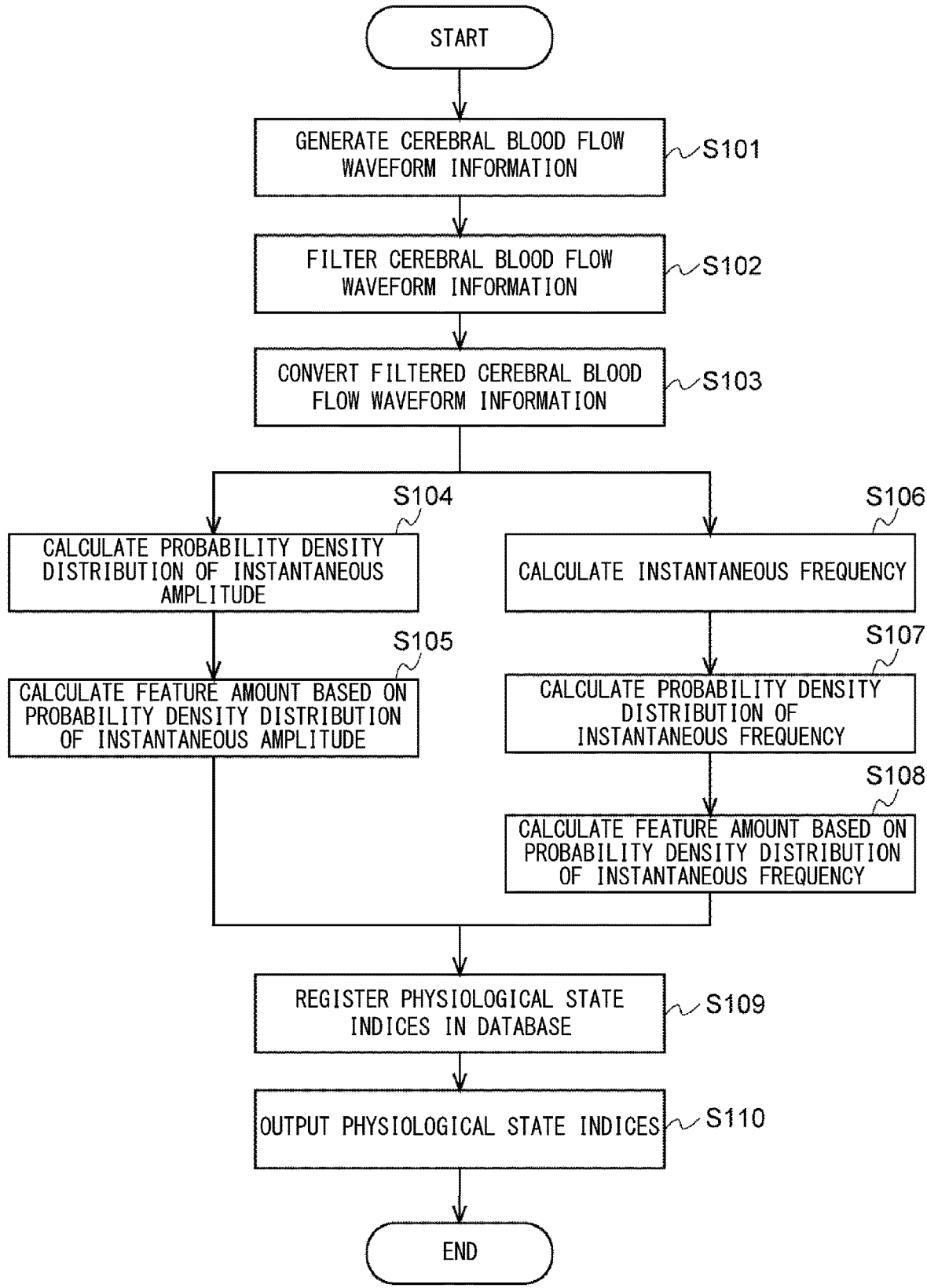
FIG. 26 is a flowchart showing one example of processing executed in the physiological state index calculation system according to one aspect of the present disclosure.

FIG. 26 is a flowchart showing one example of processing executed in the physiological state index calculation system 1 according to one aspect of the present disclosure.

In Step S101, the waveform information generation unit 101 generates cerebral blood flow waveform information using cerebral blood flow information representing the amount of the blood flow of the left brain of the living body and cerebral blood flow information representing the amount of the blood flow of the right brain of the living body, which are time series data.

In Step S102, the band-pass filter 102 filters the cerebral blood flow waveform information in the above predetermined frequency band. In Step S103, the complex number conversion unit 103 converts the filtered cerebral blood flow waveform information into a complex number.

In Step S104, the first distribution calculation unit 104 calculates the probability density distribution of the instantaneous amplitude using the converted cerebral blood flow waveform information which is the complex number. In Step S105, the first feature amount calculation unit 106 calculates the feature amount based on the probability density distribution of the instantaneous amplitude.

In Step S106, the instantaneous frequency calculation unit 105 calculates the instantaneous frequency using the converted cerebral blood flow waveform information. In Step S107, the second distribution calculation unit 107 calculates the probability density distribution of the instantaneous frequency using the instantaneous frequency. In Step S108, the second feature amount calculation unit 108 calculates the feature amount based on the probability density distribution of the instantaneous frequency.

In Step S109, the registration unit 110 registers the physiological state indices calculated in the aforementioned processing in a database. Specifically, the registration unit 110 is able to register at least one of the converted cerebral blood flow waveform information which is the complex number, the feature amount based on the probability density distribution of the instantaneous amplitude, and the feature amount based on the probability density distribution of the instantaneous frequency in a database.

In Step S110, the output unit 120 outputs the physiological state indices calculated in the aforementioned processing and the processing of FIG. 26 is ended. Specifically, the output unit 120 is able to output at least one of the converted cerebral blood flow waveform information which is the complex number, the feature amount based on the probability density distribution of the instantaneous amplitude, and the feature amount based on the probability density distribution of the instantaneous frequency.

In the aforementioned embodiment, the waveform information generation unit 101 generates, for each of parts to be measured, blood flow amount waveform information representing the amount of the blood flow of the brain of the living body, which is time series data. Next, the band-pass filter 102 filters the blood flow amount waveform information in at least one frequency band. Next, the complex number conversion unit 103 converts the filtered blood flow amount waveform information into a complex number and generates blood flow amount waveform information, which can be regarded as at least one oscillator. Then, the distribution calculation units 104 and 107 aggregate, for the at least one oscillator, the distributions of the instantaneous amplitude and the instantaneous frequency during the period in which the living body can be regarded as being in a physiologically steady state, and the feature amount calculation units 106 and 108 fit each of the distributions by a normal distribution and calculate the average value and the standard deviation of the amplitude and the frequency as feature amounts representing the physiological state. Then the output unit 120 forms the calculated feature amounts in the form of a database, and externally outputs the calculated feature amounts.

As described above, by conducting physiological experiments as described in the aforementioned embodiment using the feature amounts derived from the cerebral blood flow information of the living body and performing statistical processing as well as having the subject answer a psychological questionnaire, it is possible to capture subtle changes in a physiological state of a living body.

In the aforementioned examples, the program includes instructions (or software codes) that, when loaded into a computer, cause the computer to perform one or more of the functions described in the embodiments. The program may be stored in a non-transitory computer readable medium or a tangible storage medium. By way of example, and not a limitation, non-transitory computer readable media or tangible storage media can include a random-access memory (RAM), a read-only memory (ROM), a flash memory, a solid-state drive (SSD) or other types of memory technologies, a CD-ROM, a digital versatile disc (DVD), a Blu-ray disc or other types of optical disc storage, and magnetic cassettes, magnetic tape, magnetic disk storage or other types of magnetic storage devices. The program may be transmitted on a transitory computer readable medium or a communication medium. By way of example, and not a limitation, transitory computer readable media or communication media can include electrical, optical, acoustical, or other forms of propagated signals.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A physiological state index calculation system configured to calculate a physiological state index based on a cerebral blood flow of a living body, the physiological state index calculation system comprising:
    a band-pass filter configured to filter cerebral blood flow waveform information obtained from the cerebral blood flow in at least one frequency band, wherein
    the physiological state index calculation system converts the filtered cerebral blood flow waveform information into a complex number for at least one frequency band,
    the physiological state index calculation system is configured to calculate a distribution of instantaneous amplitude and a distribution of an instantaneous frequency which is a time differential value of an instantaneous phase, from the converted cerebral blood flow waveform information which is the complex number, and
    the shape of the distribution reflects the physiological state.

2. The physiological state index calculation system according to claim 1, wherein
    the cerebral blood flow waveform information includes first cerebral blood flow waveform information and second cerebral blood flow waveform information identified based on optical characteristics of blood, and
    the band-pass filter filters cerebral blood flow waveform information obtained by adding first cerebral blood flow waveform information and second cerebral blood flow waveform information, or filters at least one of the first cerebral blood flow waveform information and the second cerebral blood flow waveform information.

3. The physiological state index calculation system according to claim 1, wherein the information representing the cerebral blood flow is obtained by measuring the blood flow at one or more parts of the head part.

4. The physiological state index calculation system according to claim 1, wherein
    the physiological state index calculation system aggregates a real part of a logarithm of an oscillation waveform expression representing the converted cerebral blood flow waveform information, the real part corresponding to the instantaneous amplitude, during a period in which the living body can be regarded as being in a physiologically steady state to calculate a probability density distribution of the instantaneous amplitude, and
    the physiological state index calculation system is configured to approximate the probability density distribution of the instantaneous amplitude by a monomodal distribution and calculate at least one of an average value and a variance value of the distribution of the instantaneous amplitude as a feature amount.

5. The physiological state index calculation system according to claim 1, wherein the physiological state index calculation system is configured to:
    calculate an instantaneous frequency by obtaining a time differential value of an imaginary part of a logarithm of an oscillation waveform expression representing the converted cerebral blood flow waveform information,
    aggregate the instantaneous frequency during a period in which the living body can be regarded as being in a physiologically steady state and calculate a probability density distribution of the instantaneous frequency, and
    approximate the probability density distribution of the instantaneous frequency by a monomodal distribution and calculate at least one of an average value and a variance value of the distribution of the instantaneous frequency as a feature amount.

6. The physiological state index calculation system according to claim 1, wherein the frequency band includes at least one of bands of 0.4-1.5 mHz (ULF2), 1.5-4 mHz (ULF1), 4-15 mHz (VLF2), 15-40 mHz (VLF1), 0.04-0.15 Hz (LF), 0.15-0.4 Hz (HF), 0.4-1.5 Hz ($\delta 1$ waves), 1.5-4 Hz ($\delta 2$ waves), 4-8 Hz ($\theta$ waves), 8-13 Hz ($\alpha$ waves), 13-30 Hz ($\beta$ waves), and 30 Hz- ($\gamma$ waves).

7. The physiological state index calculation system according to claim 6, wherein, when the distribution of the frequency is a multimodal distribution in each frequency band with a frequency of 0.4 Hz or higher, the frequency band may be divided into a plurality of bands in such a way that the distribution of the frequency becomes a monomodal distribution.

8. The physiological state index calculation system according to claim 4, wherein the physiological state of the living body represented by the feature amount is expressed by a multidimensional space based on the number of frequency bands, the number of parts of the head to be measured, and the number of types of feature amounts.

9. The physiological state index calculation system according to claim 4, wherein the monomodal distribution is approximated by a normal distribution.

10. A physiological state index calculation method for calculating a physiological state index based on a cerebral blood flow of a living body, wherein a computer filters cerebral blood flow waveform information obtained from the cerebral blood flow in at least one frequency band, the computer converts the filtered cerebral blood flow waveform information into a complex number for at least one frequency band, the computer calculates, from the converted cerebral blood flow waveform information which is the complex number, a distribution of instantaneous amplitude and a distribution of an instantaneous frequency which is a time differential value of an instantaneous phase, and the shape of the distribution reflects the physiological state.

11. A non-transitory computer readable medium storing a physiological state index calculation program for calculating a physiological state index based on a cerebral blood flow of a living body, wherein the physiological state index calculation program causes a computer to:

filter cerebral blood flow waveform information obtained from the cerebral blood flow in at least one frequency band;

convert the filtered cerebral blood flow waveform information into a complex number for at least one frequency band; and calculate, from the converted cerebral blood flow waveform information which is the complex number, a distribution of instantaneous amplitude and a distribution of an instantaneous frequency which is a time differential value of an instantaneous phase, and the shape of the distribution reflects the physiological state.

* * * * *